(12) United States Patent
Wu

(10) Patent No.: US 10,633,691 B2
(45) Date of Patent: Apr. 28, 2020

(54) METHODS TO PROFILE MOLECULAR COMPLEXES OR SINGLE CELLS VIA PROXIMITY DEPENDANT BARCODING

(71) Applicant: Di Wu, Solna (SE)

(72) Inventor: Di Wu, Solna (SE)

( * ) Notice: Subject to any disclaimer, the term of this patent is extended or adjusted under 35 U.S.C. 154(b) by 1084 days.

(21) Appl. No.: 15/021,282

(22) PCT Filed: Sep. 30, 2014

(86) PCT No.: PCT/SE2014/051133
§ 371 (c)(1),
(2) Date: Mar. 11, 2016

(87) PCT Pub. No.: WO2015/047186
PCT Pub. Date: Apr. 2, 2015

(65) Prior Publication Data
US 2016/0281134 A1  Sep. 29, 2016

(30) Foreign Application Priority Data
Sep. 30, 2013 (SE) ........................... 1351137

(51) Int. Cl.
| | | |
|---|---|---|
| *C12Q 1/68* | (2018.01) | |
| *C12Q 1/6806* | (2018.01) | |
| *C12Q 1/6827* | (2018.01) | |
| *C12Q 1/6874* | (2018.01) | |

(52) U.S. Cl.
CPC ......... *C12Q 1/6806* (2013.01); *C12Q 1/6827* (2013.01); *C12Q 1/6874* (2013.01)

(58) Field of Classification Search
None
See application file for complete search history.

(56) References Cited

U.S. PATENT DOCUMENTS

| | | | | |
|---|---|---|---|---|
| 7,632,642 B2 * | 12/2009 | Wangh | ............... | C12Q 1/6844 435/6.13 |
| 2012/0220494 A1 * | 8/2012 | Samuels | ............ | C12N 15/1075 506/16 |

FOREIGN PATENT DOCUMENTS

| | | | |
|---|---|---|---|
| WO | 2012/112804 A1 | 8/2002 | |
| WO | 2012042374 | 4/2012 | |
| WO | 2012048341 | 4/2012 | |
| WO | 2012106385 | 8/2012 | |
| WO | WO-2012106385 A2 * | 8/2012 | ........... C12Q 1/6816 |

OTHER PUBLICATIONS

International Search Report PCT/SE2014/051133 dated Jan. 19, 2015.
Ulf Landegren et al., "Molecular tools for a molecular medicine: analyzing genes, transcripts and proteins using padlock and proximity probes", 2004, vol. 17; Abstract.
Jonas Binladen et al., "The use of coded PCR primers enables high-throughput sequencing of multiple homolog amplification products by 454 parallel sequencing", 2007, Feb. vol. 197, p. 1-9; Abstract.
Hindson et al., "High-Throughput Droplet Digital PCR System for Absolute Quantitation of DNA Copy Number", Analytical Chemistry, 2011, 83, 8604-8610.

* cited by examiner

*Primary Examiner* — Tracy Vivlemore
*Assistant Examiner* — Sahana S Kaup
(74) *Attorney, Agent, or Firm* — Young & Thompson

(57) ABSTRACT

Method for studying constituents of individual molecular complexes by labelling the molecules belonging to the same complex with at least one set of molecular constructs, wherein each set member includes a Unique Identifying Sequence (UIS), which is a nucleic acid sequence unique for each set member, and at least one Common Tag Sequence (CTS), which is a nucleic acid sequence common to all set members, by: attaching the molecular construct to the complex by ligating or hybridizing the molecular construct to a nucleic acid molecule of the complex, or ligating or hybridizing the tag to a nucleic acid linked to an affinity binder that binds specifically to a constituent of the complex; labelling the molecules belonging to the same complex using the molecular construct tags as primers or templates in a nucleic acid polymerization reaction; and analyzing the composition of the complex by analyzing combinations of UISs and CTSs.

12 Claims, 17 Drawing Sheets
Specification includes a Sequence Listing.

METHODS TO PROFILE MOLECULAR COMPLEXES OR SINGLE CELLS VIA PROXIMITY DEPENDANT BARCODING

FIELD OF THE INVENTION

The present invention relates to methods in molecular biology, and in particular to methods for studying complexes of molecules such as DNA, RNA, and proteins, or studying these molecules in single cells.

BACKGROUND OF THE INVENTION

Currently there are several technologies available to study molecular complexes, e.g. protein complexes, protein-DNA complexes. Co-Immunoprecipitation (Co-IP) uses different capturing antibodies and detecting antibodies to analyse the interacting protein complex. Proximity ligation assay (PLA) or proximity extension assay (PEA) employs the idea that only when two or more affinity probes bind to adjacent or interacting proteins, the attached DNA oligonucleotides conjugated on the antibody are brought into proximity and thus allowing an enzymatic ligation or extension and formation of a new amplifiable reporter DNA molecule. In the chromatin immunoprecipitation sequencing (ChIP-seq), antibodies are used to capture the protein of interest with its associated DNA fragments. Then the DNA fragments are sequenced to reveal where the protein binds on the chromatin.

These methods have provided useful knowledge when studying the biological regulation at molecular level. However all these methods have the limitation of being unable to identify and quantify all the components from each individual complex, specifically to profile the said complexes. For example, Chip-seq is able to reveal where a protein binds to the chromatin, but it cannot reveal whether two or more proteins bind simultaneously to the same region on the chromatin.

For single cell studies, flow cytometer allows the cells flowing through a thin channel and detects the signal from single cells one by one at a speed as high as several thousand cells per second. To analyse several proteins in parallel, different antibodies can be labelled with different fluorophore. However, spectral overlap can arise when many fluorescent signals are detected simultaneously. To avoid this problem, the mass cytometer, by using mass isotopes to label antibodies, can analyse more than 30 proteins with minimal signal overlap. However, the multiplexing capacity is still limited in the flow-based measurements, and they are not yet suitable for nucleic acid analysis. One way to achieve highly multiplexed analysis for single cells is by sorting cells into separated reaction wells, and analyse the components of each single cell separately. For example in single cell RNA-Seq, single cells are sorted into single wells manually or with the help of automation e.g. fluorescence activated cell sorting (FACS), followed by cell lysis, reverse transcription (RT) and sequencing library preparation with sample barcodes. Then the barcoded products of different cells can be pooled together and sequenced by next generation sequencing (NGS). By this procedure, it's possible analyse several hundreds of cells, but it would be still very laborious to sort many single cells, e.g. more than 10 000, and perform the following library preparation individually. Even with automation system, like C1™ Single-Cell Auto Prep System, preparing the sequencing library of many cells is still a difficult task.

WO2012/042374 aims to provide a method for determining the number or concentration of a molecule in a sample, using nucleic acid molecule tags with unique sequences.

Hindson et al, *Analytical Chemistry*, 2011, 83, 8604-8610 disclose a high throughput droplet digital system for absolute quantitation of DNA copy number.

WO2012/048341 aims to provide methods and compositions for high-throughput, single cell analyses are provided. The methods and compositions can be used for analysis of genomes and transcriptomes, as well as antibody discovery, HLA typing, haplotyping and drug discovery.

Binladen et al. (PLoS ONE 2(2): e197) used conventional PCR with 59-nucleotide tagged primers to generate homologous DNA amplification products from multiple specimens, followed by sequencing through a high-throughput DNA Sequencing System. Each DNA sequence was subsequently traced back to its individual source through 59tag-analysis.

Landegren et al. (J. Mol. Recognit. 2004; 17: 194-197) discuss using a set of ligation-based reagents termed padlock probes and proximity ligation probes to meet challenges relating to specific detection of all the macromolecules that are being identified in the course of genome projects. The probes include elements with affinity for specific nucleic acid and protein molecules, respectively, along with unique identifier DNA sequence elements that encode the identity of the recognized target molecules.

SUMMARY OF THE INVENTION

This invention employs the concept that the molecules belonging to the same molecular complex or cells are in proximity, so that they have a higher chance to be barcoded by the same or the same set of unique identifying sequences (UIS).

The method described herein uses one or several UISs to label an oligonucleotide of each of the components belonging to the same molecular complex. The oligonucleotides belonging to the same complex (in proximity) will be barcoded by the same or the same set of UISs. After sorting all the sequenced reads using the UISs, and analysing the identity of the associated sequences, the molecular components of each complex can be identified.

In brief, the invention relates to a method for studying constituents of a molecular complex by labelling the molecules belonging to the same complex with at least one set of molecular constructs, wherein each member of each set, comprises a Unique Identifying Sequence (UIS), which is a nucleic acid sequence unique for each member of the set, and at least one Common Tag Sequence (CTS), which is a nucleic acid sequence common to all members of the set, by:
  attaching the molecular construct to the complex by ligating or hybridizing the molecular construct to a nucleic acid molecule of the complex, or ligating or hybridizing the molecular construct to a nucleic acid linked to an affinity binder that binds specifically to a constituent of the complex;
  labelling all the molecules, belonging to the same complex by using the molecular constructs as primers or templates in a nucleic acid polymerisation reaction, and
  analysing the composition of the molecular complex by analysing the combinations of UISs and CTSs, and if applicable the nucleic acid sequences of the constituents.

The method according to the invention has the advantage to give a combinatorial profile of all the molecules in the complex rather than identifying the binding pairs of two molecules from each complex in the prior art methods.

The method according to the invention can be applied to profile any molecular complex comprising oligonucleotides e.g. DNA complex, or complex whose components can be labelled with oligonucleotides via affinity binders, e.g. protein complex, protein-DNA complex and also these molecules or complexes in micro vesicles or single cells.

To make general procedure described above work, several preferred embodiments of the invention are set out in the dependent claims and described in the drawings.

SHORT DESCRIPTION OF THE APPENDED TABLE AND DRAWINGS

Table 1 describes the oligonucleotides used in FIG. 1-12. N=a degenerate base (A or T or G or C).

Figure 8:
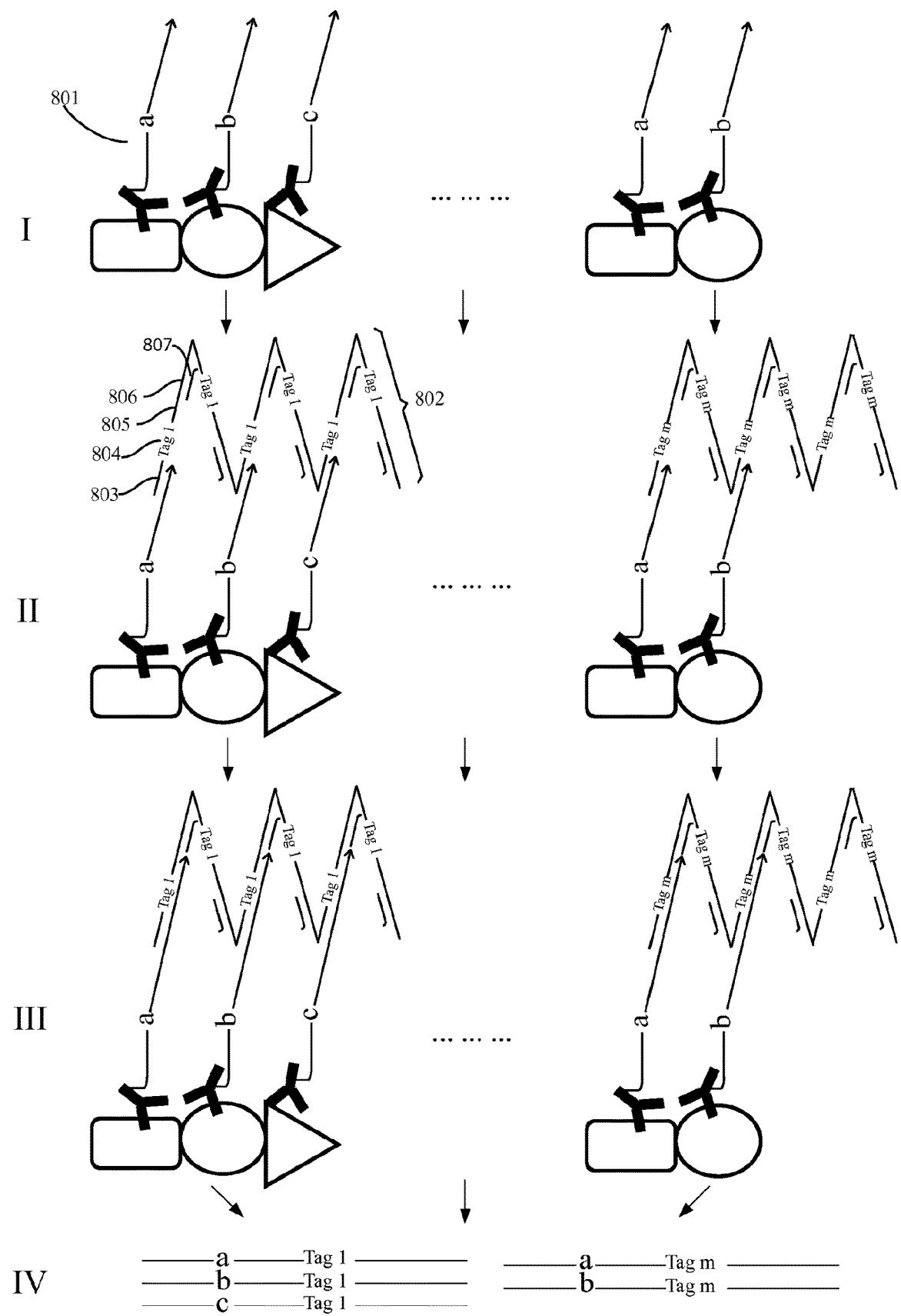
FIG. 8 illustrates a second example of the embodiment described in FIG. 6.
Figure 16:
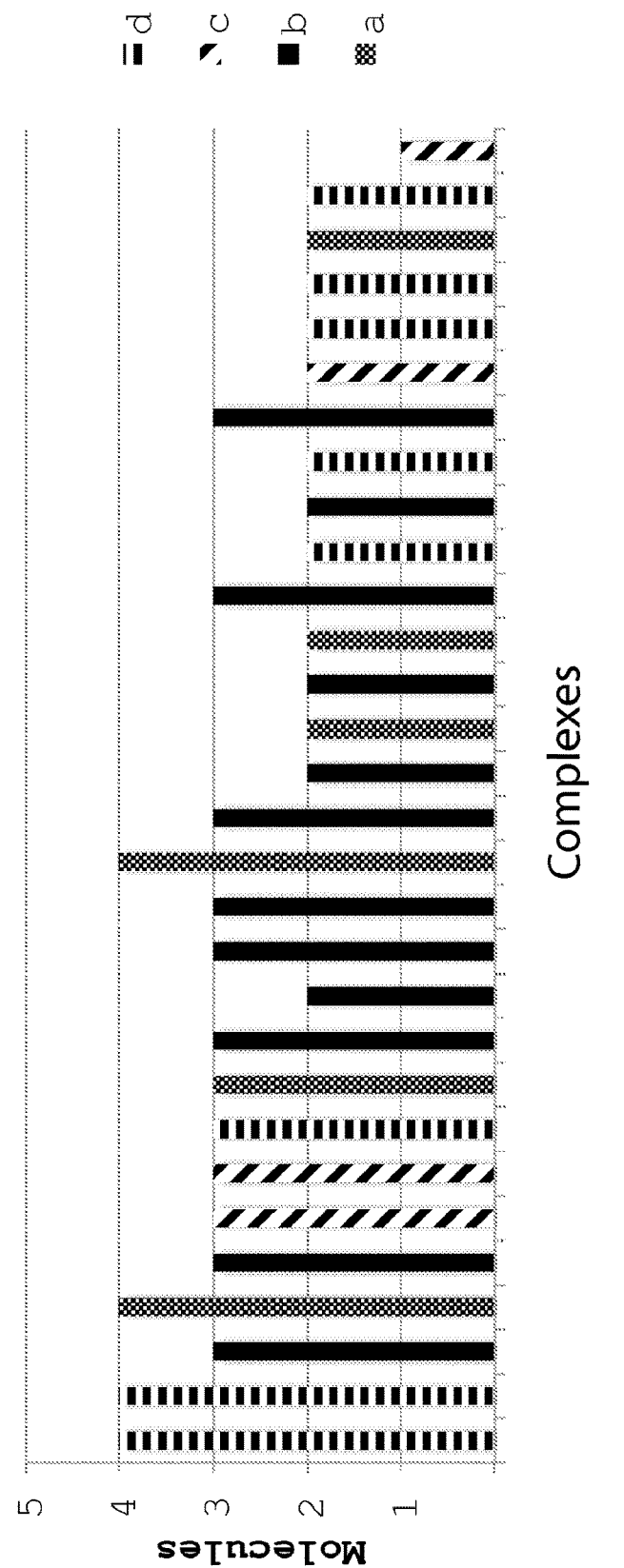

FIG. 16 further illustrates the result from FIG. 8.

Figure 11:
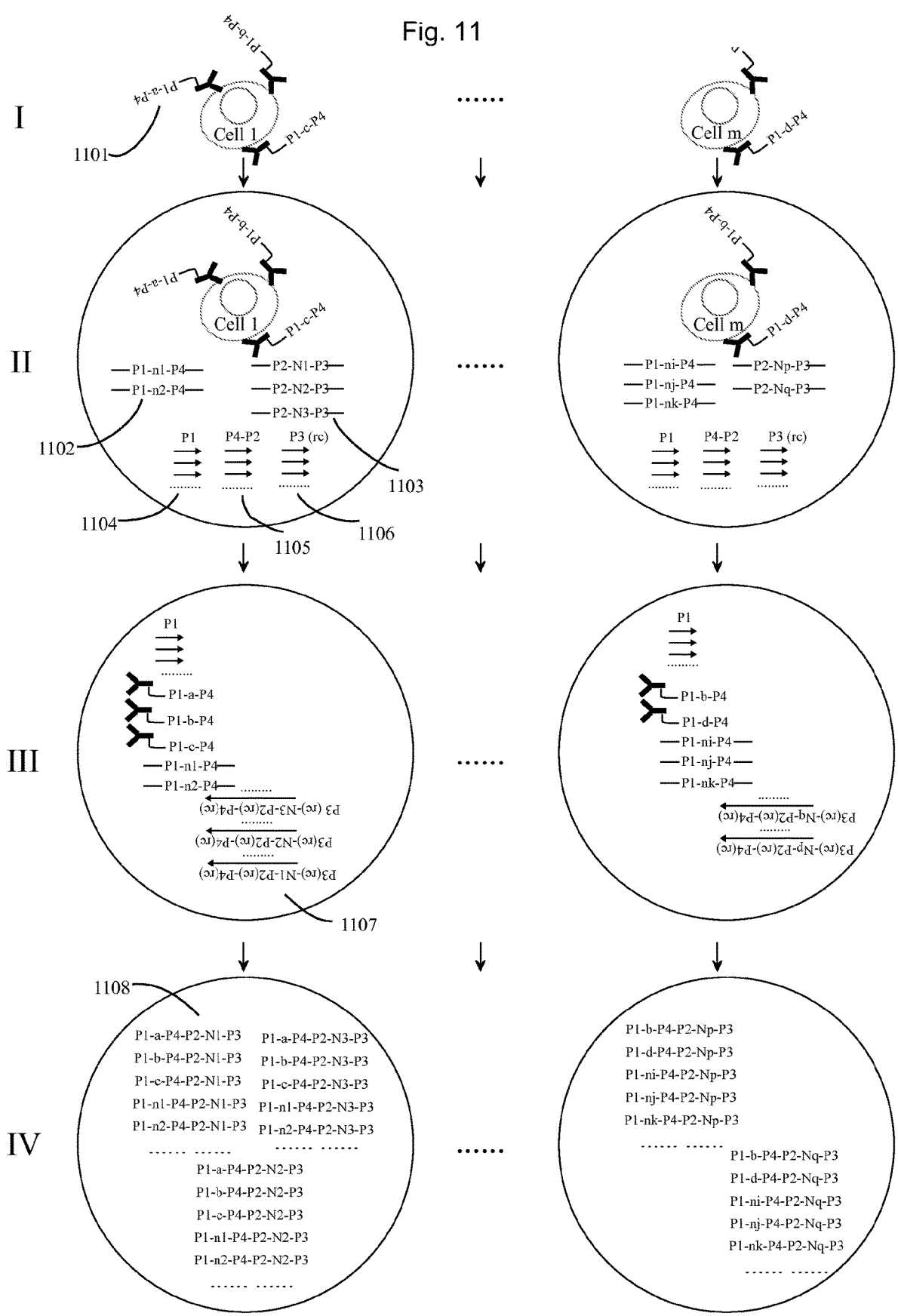
FIG. 11 illustrates an example of using the embodiment described in FIG. 10.
Figure 17:
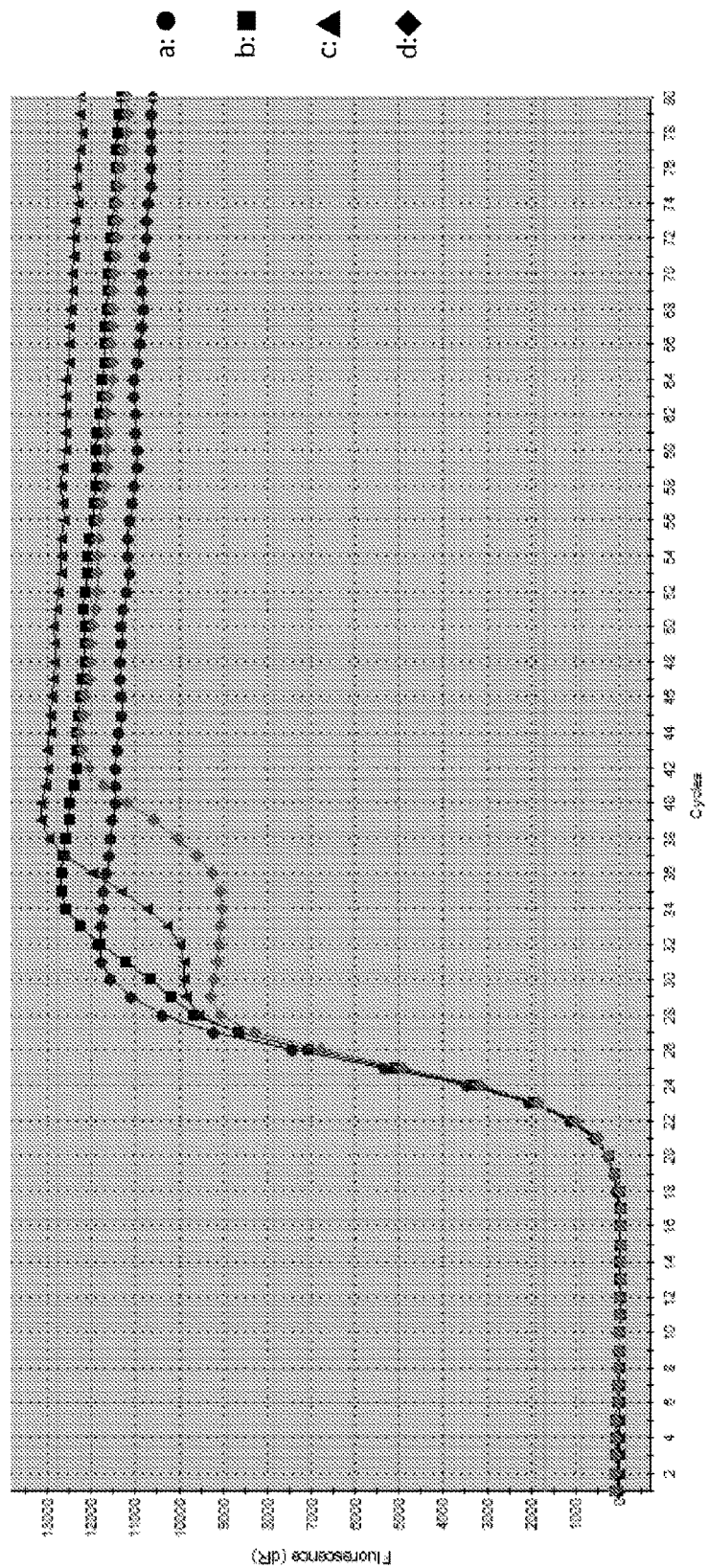

FIG. 17 illustrates the result from FIG. 11.

DEFINITIONS

The term "molecular complex" refers to any entity whose components comprising oligonucleotides, or can be labelled with oligonucleotides.

The term "Affinity binder" shall be construed as any molecular entity capable of selectively binding to an analyte of interest. Affinity binders may be polyclonal or monoclonal antibodies, fragments thereof such as F(ab')$_2$, Fab, Fab', Fv, Fc, and Fd fragments, which may be incorporated into single domain antibodies, single-chain antibodies, maxibodies, minibodies, intrabodies, diabodies, triabodies, tetrabodies, v-NAR and bis-scFv. Affinity binders also include binding molecules such as lectins, streptavidin, biotin, receptor and enzyme ligands and analogs thereof, molecularly imprinted polymers, affibodies or any other affinity binder. If the analyte of interest is a nucleic acid, the affinity binder may be a nucleic acid capable of hybridizing to the analyte nucleic acid. In the aspects of the invention using antibodies, the antibodies may be substituted for other types of affinity binders as applicable.

Affinity between two entities means an affinity of at least $10^6$, $10^7$, $10^8$ $10^9$ M$^{-1}$, or $10^{10}$ M$^{-1}$. Affinities greater than $10^8$ M$^{-1}$ are preferred.

The term "antibody" refers to an intact antibody, or a binding fragment thereof. An antibody may comprise a complete antibody molecule (including polyclonal, monoclonal or chimeric), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136).

The term "tag" refers to a nucleic acid molecule, e.g. DNA, RNA.

The term "labelling" of a molecule refers to the association of a known nucleic acid sequence (the "label") to the molecule to be labelled which facilitates the identification and/or the quantitation of the molecule by sequencing or other identification of the nucleic acid. The molecule to be labelled and the nucleic acid label may be physically connected, e.g. by a chemical bond, or physically unconnected as long as the molecule and the label can be unambiguously associated with each other.

DETAILED DESCRIPTION OF PREFERRED EMBODIMENTS OF THE INVENTION

As stated above, the invention relates to a method for studying constituents in a molecular complex by labelling the molecules belonging to the same complex with at least one set of molecular constructs, wherein each member of each set comprises a Unique Identifying Sequence (UIS) and a Common Tag Sequence (CTS) by:

attaching the molecular construct tag to the complex, labelling the molecules belonging to the same complex by using the molecular constructs as primers and templates in a nucleic acid polymerization reaction, analysing the composition of the molecular complex by analysing the combinations of UISs, CTSs and if applicable the nucleic acid sequences of the constituents.

The invention will now be described with reference to the figures.

Figure 1:
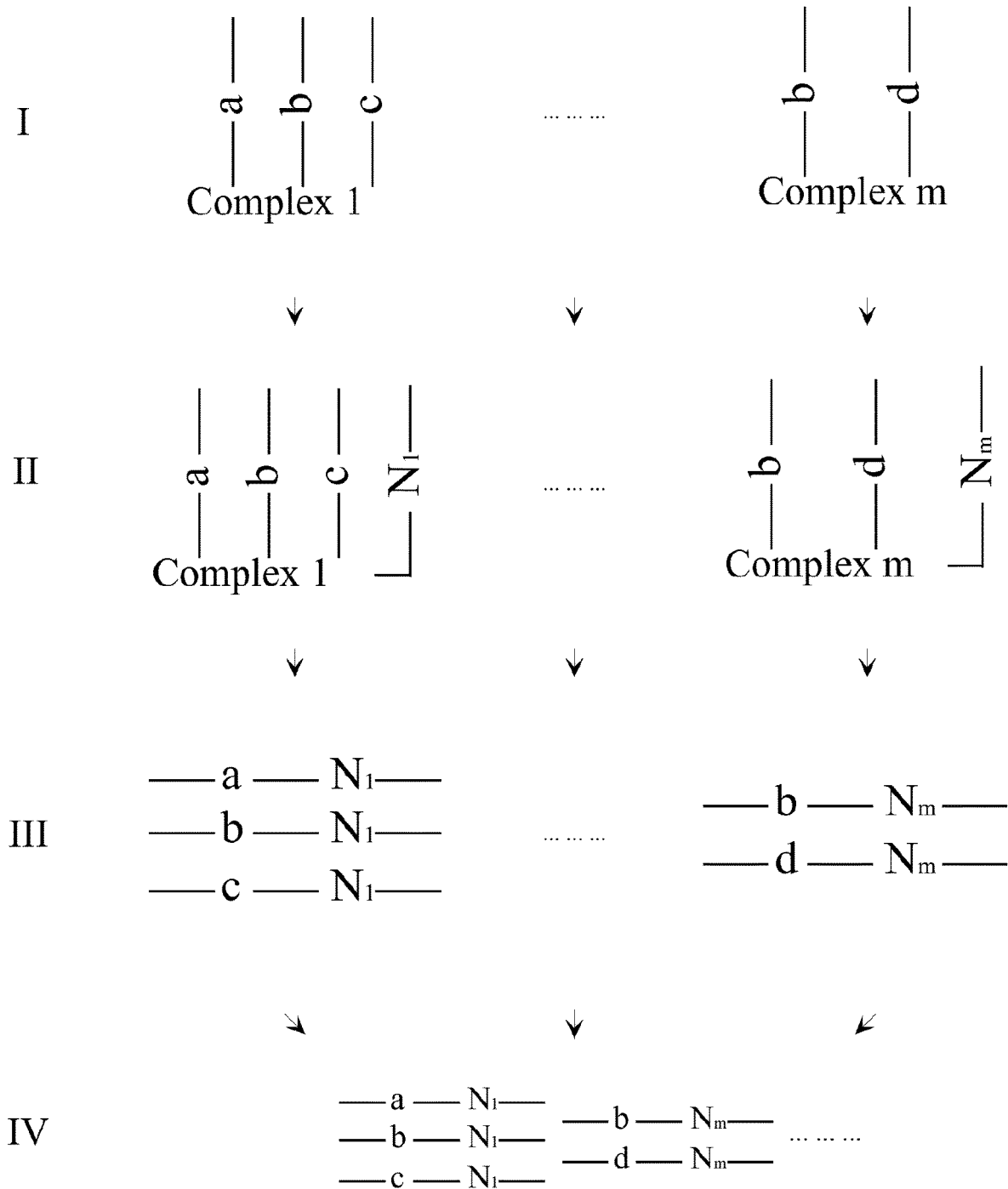
FIG. 1 is an illustration of a first embodiment of the invention.

FIG. 1 illustrates a method of labelling all the components of a complex with identical and unique tags by repeatedly using a unique tag attached to the complex.

I. The complexes to be analysed comprise molecules, also called constituents of the complex, each such constituent containing a nucleic acid molecule sequence, e.g. DNA, RNA, or components that can be labelled with such a nucleic acid molecule sequence, e.g. proteins that can be labelled by antibodies conjugated with a nucleic acid molecule sequence. Complex 1 comprises nucleic acid sequences a, b and c; complex m comprises nucleic acid sequences b and d.

II. Then each complex is attached to a molecular construct containing a Unique Identifying Sequence (UIS), e.g. a 15-mer of degenerate bases. The complex 1 is attached to a tag comprising the UIS $N_1$ and complex m is attached to a tag comprising the UIS $N_m$. III. Then the tag for each complex is used repeatedly to label all the nucleic acid sequences belonging to that complex, such that all the nucleic acid sequences of the same complex are labelled with an identical UIS. The a, b and c in complex 1 are all labelled with the UIS $N_1$, and b and d in complex m are all labelled with the UIS $N_m$. IV. Then all the labelled oligonucleotides are sequenced. Each sequencing read contains the nucleic acid sequence from the complex, indicating the identity of the component, and also the UIS indicating from which complex it originates. By sorting all the reads by the UISs, and analysing the coupled identity sequence, all the components of each complex can be decoded.

Figure 2:
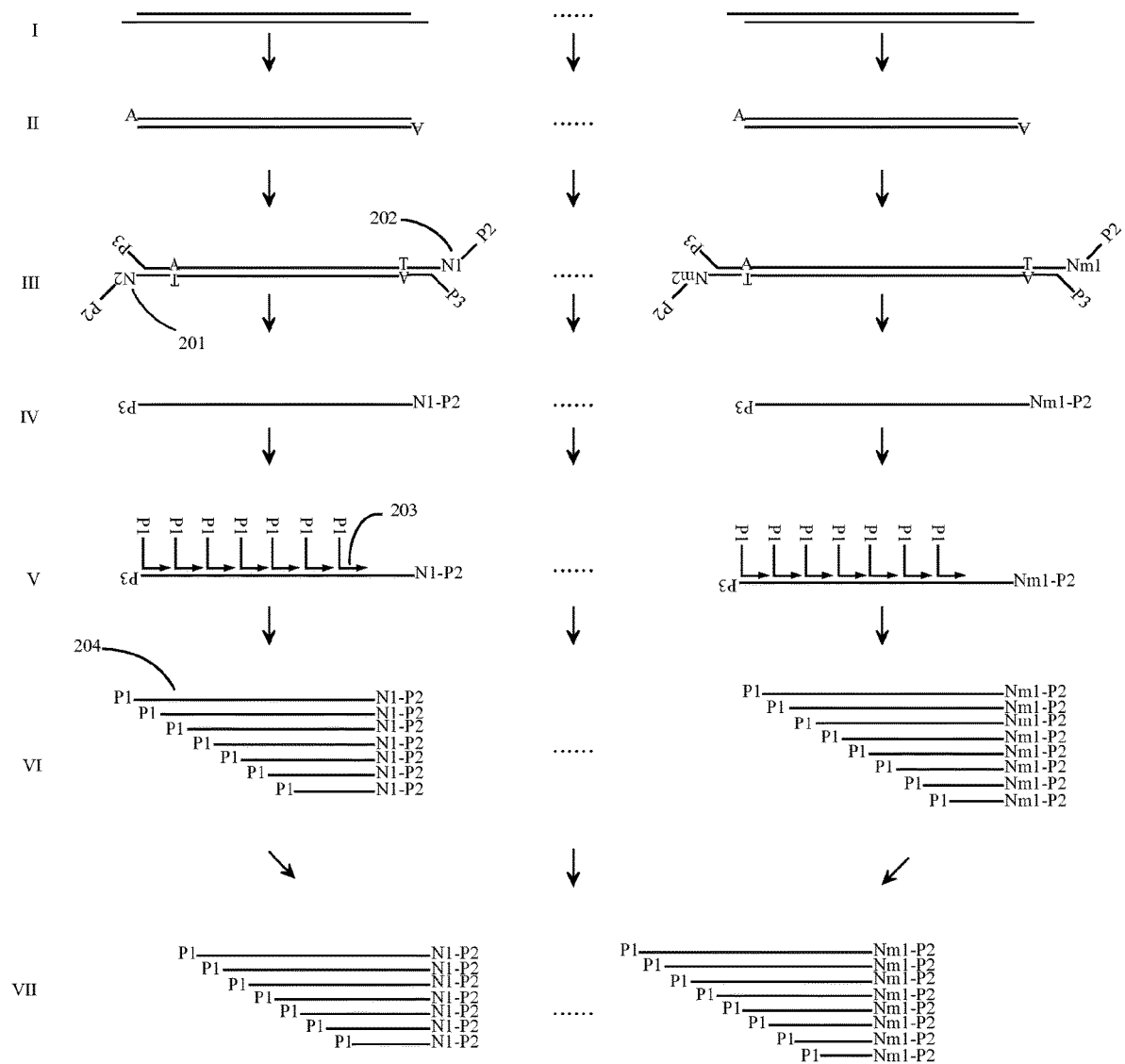
FIG. 2 illustrates an example of using the embodiment described in FIG. 1.

FIG. 2 illustrates an example of using the method described in FIG. 1 to obtain the sequence of long DNA molecules.

I and II. DNA molecules comprising several thousand base pairs are first end repaired and dA-tailed. III. Each DNA is labelled with a unique tag on its 5'-end by being ligated with a molecular construct (201,202) containing degenerate bases forming an UIS and a Common Tag Sequence (CTS) serving as primer hybridization sites. DNA 1 is labelled with a tag comprising UIS $N_1$, and DNA m is labelled with a tag comprising UIS $N_m$. Both tags comprise the CTS denoted P2. A further primer hybridization sequence P3 is ligated to the 3'-end of each DNA. IV. The DNA is then amplified by using primers of P2 and P3. By using excess of P2 (or P3) the PCR products are dominated by single strand DNA. V. The single strand PCR products are hybridized by primers with a common 5'-end denoted P1 and degenerative bases at the 3'-end (203), e.g. random 6-mer, such that the primers hybridize on the single strand DNA on multiple sites. VI. Then a DNA polymerization reaction by using DNA polymerase with strand displacement activity is carried out, such that the extension products on the same single strand DNA contain different sequences next to the 5'end and identical UIS next to the 3'-end. The extension products (204) from the extension product of DNA 1 all have the same UIS $N_1$ next to the 3'-end; and the extension products from the PCR product of DNA m all have the same UIS $N_m$ next to the 3'-end. VII. All the extension products can be amplified by primer P1 and P2 and sequenced from both ends. Sorting the sequencing reads by using the UISs, all the extension products from the same DNA can be put together, each carrying a different 5'-end sequence, depending on where the extension has started on the DNA. Then the 5'-end sequences can be mapped together to obtain the original DNA molecule sequence.

A detailed example of experimental protocol comprises:

Ligating UIS to DNA

The genomic DNA was sheared and size selected on 1.5% agarose gel to retrieve the band around 2000 bp and the DNA was extracted using Gel Extraction Kit (Qiagen). The DNA is end repaired using NEBNext® End Repair Module (NEB). The end-repaired products are dA-tailed using NEB Next dA-Tailing Module (NEB). Then the products are ligated with adapters (oligo 1 and oligo 2, both 500 nM) using NEB Quick Ligation™ Kit (NEB). The ligated products were size selected to remove the ligated adapter dimmer by using E-gel (Life technologies).

Amplifying the Ligated Products and Barcoding

The ligation products were amplified by PCR using the program as 95° C. for 2 min followed by 30 cycles of 95° C. 30 s, 55° C. 1 min, 72° C. 3 min, using one primer (oligo 3) at the concentration of 500 nM, and the other primer (oligo 4) at the concentration of 100 nM to favour the PCR products to be single strand DNA. The PCR products were purified and size selected. Then the purified PCR products were hybridized by primers (oligo 5, 500 nM) containing degenerate bases at the 3'-end. Then dN(A,T,G,C)TP (200 μM) and Bst polymerase (1 unit) were spiked into the mix, and then put into a thermal cycler at the program at 10° C. 45 s, 20° C. 45 s, 30° C. 45 s, 40° C. 45 s, 50° C. 45 s, 65° C. 5 min.

Library Preparation and Sequencing

The extension products were amplified by PCR using the program as 95° C. for 2 min followed by 20 cycles of 95° C. 30 s, 55° C. 1 min, 72° C. 3 min using the primers at the concentration of 500 nM (oligo 3 and oligo 6). The PCR products were purified and ligated with adapters (Illumina) and sequenced using pair-end sequencing on HiSeq (Illumina).

Figure 3:
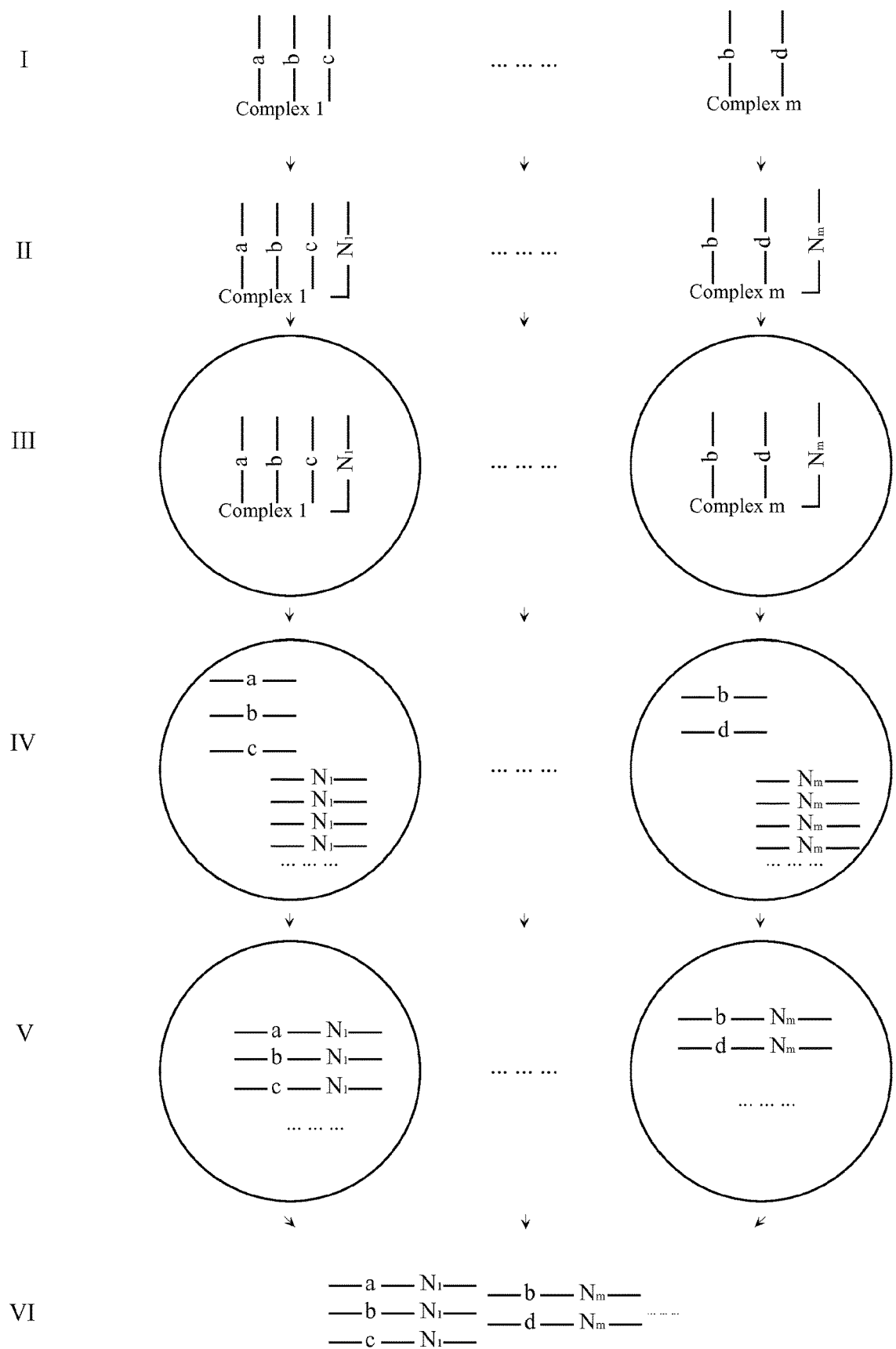
FIG. 3 is an illustration of a second embodiment of the invention.

FIG. 3 illustrates a method of labelling all the components of a complex with identical and unique tags by using amplification products of a unique tag attached the complex in a confined volume.

I. The complexes to be analysed comprise complex constituents each such constituent containing a nucleic acid molecule sequence, e.g. DNA, RNA, or components that can be labelled with such an first UIS nucleic acid molecule sequence, e.g. proteins that can be labelled by antibodies conjugated with a nucleic acid molecule sequence. Complex 1 comprises UISs a, b and c; complex m comprises UISs b and d. II. Then each complex is attached to a molecular construct containing a second Unique Identifying Sequence, e.g. a 15-mer of degenerate bases. The complex 1 is attached to a second UIS $N_1$ and complex m is attached to a second UIS $N_m$. III. Then the complexes together with their attached second UISs are put into droplets, e.g. water in oil emulsions, such that each droplet contains 0 or 1 complex. IV. Then the molecular construct, comprising the second UIS, in each droplet is amplified by emulsion PCR in each droplet. V. After sufficient PCR cycles, the amplified products of the molecular construct comprising the second UIS could serve as primers to extend on the nucleic acid sequences of the constituents of the complex in the same droplet, such that all the first UISs on the complex in each droplet are all labelled with the same second UIS. The a, b, c of complex 1 are all labelled with the second UIS $N_1$, and the b, d of complex m are all labelled with The second UIS $N_m$. VI. The extension products from all the droplets are retrieved and sequenced. Each sequencing read contains a first UIS, indicating the identity of the component, and also a second UIS indicating from which complex it originates. By sorting all the reads by the second UIS, and analyzing the coupled first UIS, all the components of each complex can be decoded.

Figure 4:
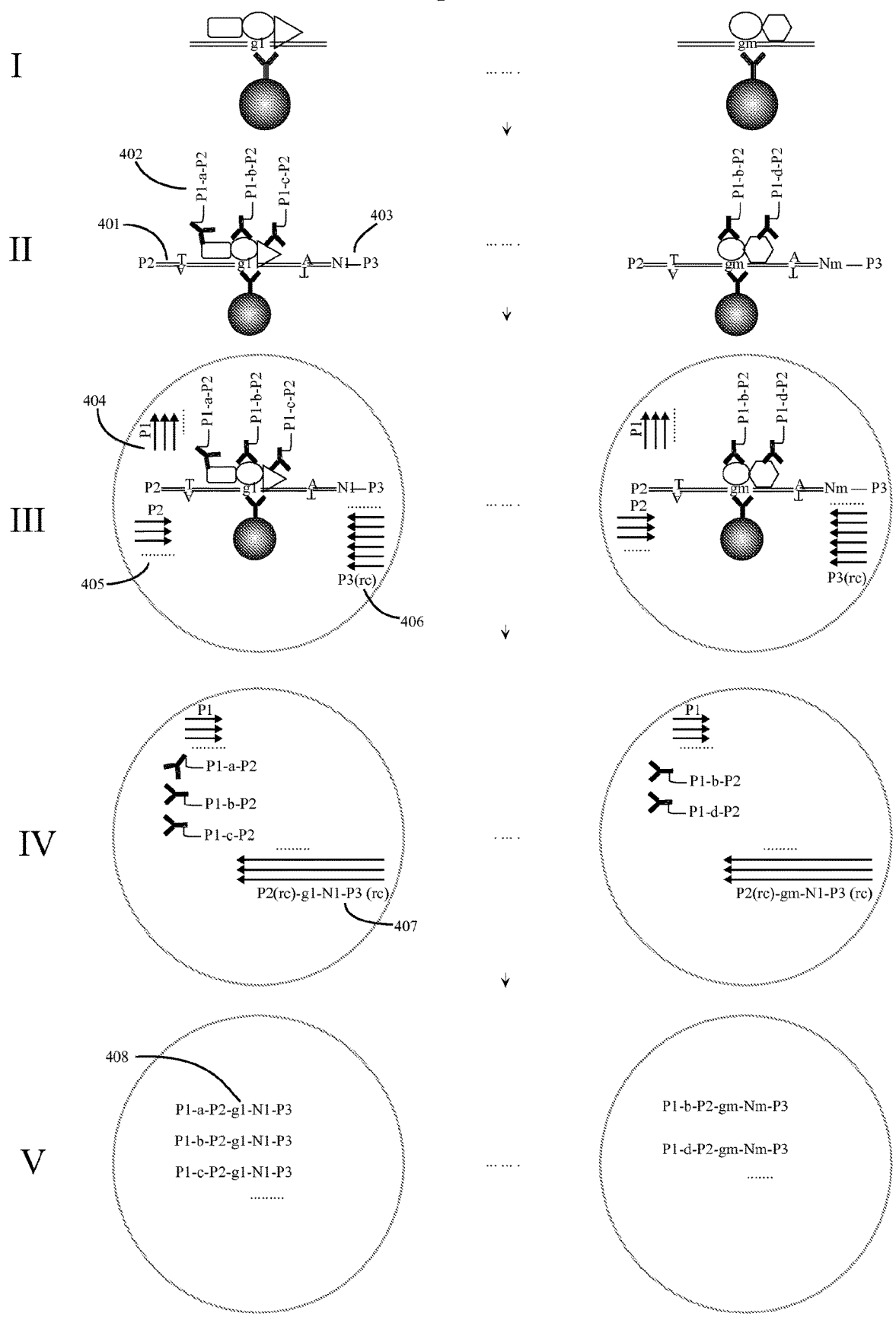
FIG. 4 illustrates an example of using the embodiment described in FIG. 3.

FIG. 4. Illustrates an example of using the method of FIG. 3 to profile protein-DNA complexes.

I. Each protein-DNA complex contains one genomic DNA fragment and proteins bound to it. The complex 1 consist of genomic DNA fragment $g_1$ and protein A, B, C, and complex m consist of genomic DNA fragment $g_m$, and protein B, D. II. Each genomic DNA fragment is ligated with two adapters on its two ends, one (401) contains a P2 primer binding site at the 5'-end, and the other being a first set of molecular construct (403) containing a CTS primer binding site (denoted P3) at the 3'-end and also a unique sequence tag comprising a first UIS. For example, the genomic DNA fragment of complex 1 is ligated with tags containing UIS $N_1$, and the genomic fragment of complex m is ligated with adapters containing UIS $N_m$. Then the proteins on each complex are probed by antibodies conjugated with a second set of molecular construct (402) containing universal 5' and 3'-ends as P1 and P2 (also called Common Tag Sequences "CTS") and also a second UIS as a, b, c, and d. The first set of molecular construct tags comprise subsets wherein the members of each subset comprise a first UIS ($N_x$) and a CTS P3, serving as a primer binding site. The second set of molecular construct tags thus comprise subsets of tags for each protein A, B, C, and D, wherein the members of each subset comprise an affinity binder binding specifically to a specific protein (A, B, C, or D, respectively), a Common Tag Sequence (CTS) P1, serving as a primer binding site, a Unique Identifying Sequence ("UIS") a, b, c, or d, corresponding to the protein A, B, C, or D, respectively, and a further CTS P2, also serving as a primer binding site. III. Then each protein-DNA complex with the bound antibody-oligonucleotide conjugates and the ligated adapters/tags are put into a droplet, such that each droplet contains 0 or 1 complex. In each droplet, there are PCR reagents comprising DNA polymerase and 3 different sets of DNA primers, as P1 (404), P2 (405) and P3 (rc) (406). IV. The genomic DNA fragment with its adapters can be amplified by the primers of P2 and P3 (rc) in the droplet. After sufficient PCR cycles, and by using excess of primer P3 (rc), the PCR products are single strand DNA (407) containing the genomic fragment sequence, the first UIS, and also a universal 3'-end, which is complementary to the 3'-end of the nucleic acid part of the molecular construct of the second set. V. Then the single strand PCR products from IV can extend on the nucleic acid part of the second molecular construct, such that all the nucleic acid parts of the second molecular construct comprising the second UIS, in one droplet are labelled with the same first UIS and the genomic fragment sequence (408). The a, b, c from the complex 1 in one droplet all obtain the same genomic DNA sequence $g_1$ and UIS $N_1$, and b, d from the complex m in another droplet all obtain the same genomic sequence $g_m$, and UIS $N_m$. After sequencing, by sorting all the reads by the first UIS and the associated gnomic DNA sequence and second UIS, the proteins and genomic DNA fragment can be mapped together.

The reaction is preferably performed on a solid support for the ease of changing buffer and removing unbound material, e.g. adapters, antibody-oligonucleotides. Since the complexes need to be put in droplets, the solid supports should be able to be separated, e.g. beads. It's also possible to release the complexes from the solid support if using reversible immobilization of capturing antibody (using photo cleavable biotin). Releasing the complexes from the solid support can avoid the risk that the two complexes are on the same solid support causing false positive interactions.

A detailed example of experimental protocol comprises:

Preparing Antibody-Oligonucleotide Conjugates

Each antibody (13.3 µM, 10 µl) was activated by adding 1 µl of NHS-easter crosslinker (5 mM) in DMSO at room temperature for 30 minutes. The activated antibody was purified by running through a Zeba column according to the manufacturer's protocol (Thermo Scientific). The purified antibody was mixed with 3 µl, 100 µM 5'Azide modified oligonucleotides (one of oligo 48-55, or oligo 21) and incubated at 4° C. overnight. The antibody-oligonucleotide conjugates are kept at 4° C. before use.

Preparing Capturing Beads

The antibody-oligo 21 conjugates (100 nM, 100 ul) were incubated with 1 mg streptavidin modified beads (Life Technologies) at room temperature for 1 hour, followed by washing twice with 1×PBS with 0.05% Tween 20 (PBST).

Chromatin Immunoprecipitation

The cells were cross-linked by adding formaldehyde (1%) and incubated at RT for 10 minutes. The crosslinking reaction was stopped by adding glycine (0.125M) and incubated at RT for 5 minutes. The cells were scraped from dishes into 1×PBS and concentrated by centrifuge. The cells were resuspended into 1 ml cell lysis buffer and incubated on ice for 10 minutes. The cells were centrifuged to pellet the nuclei. The nuclei were resuspended in 200 µl nuclei lysis buffer and incubated on ice for 10 minutes. The chromatin was sonicated to an average length of around 400 bp. The chromatin was incubated with the capturing beads at 4° C. overnight.

Adapter Ligation and Probe Binding

The bound DNA on beads were end repaired by the NEBNext End Repair Module and dA-tailed by using NEB Next dA-Tailing Module (NEB). After washing twice with PBST, 50 µl of 1× Quick Ligation Reaction Buffer (NEB) containing 500 nM adapters (oligo 56 and 57), 1 unit Quick T4 DNA Ligase was added and incubated at 20° C. for 15 minutes. After washing twice with 100 µl PBST, 50 µl of antibody dilution buffer (Olink) containing antibody-oligonucleotides conjugates, each at the concentration of 1 nM, was added and incubated at 37° C. for 2 hours.

Releasing Complexes from Beads and Emulsion PCR

After washing twice with PBST, 50 µl of 1×ddPCR Supermix for Probes (Bio-rad) containing 100 forward primer1 (oligo 3), 25 nM forward primer 2 (oligo 58), and 100 nM reverse primer (oligo 6) was added. Then the complexes were released from beads by being exposed to UV light (360 nm) at room temperature for 15 minutes. Then the supernatant was removed from the beads and carried out for the emulsion PCR as 95° C. for 10 minutes and 60 cycles of 95° C., 15 seconds, 60° C. 1 minute. Then the droplets were destroyed and the PCR products were extracted.

Sequencing

The PCR products were purified and ligated with adapters (Illumina) and sequenced using pair-end sequencing on HiSeq (Illumina).

Figure 5:
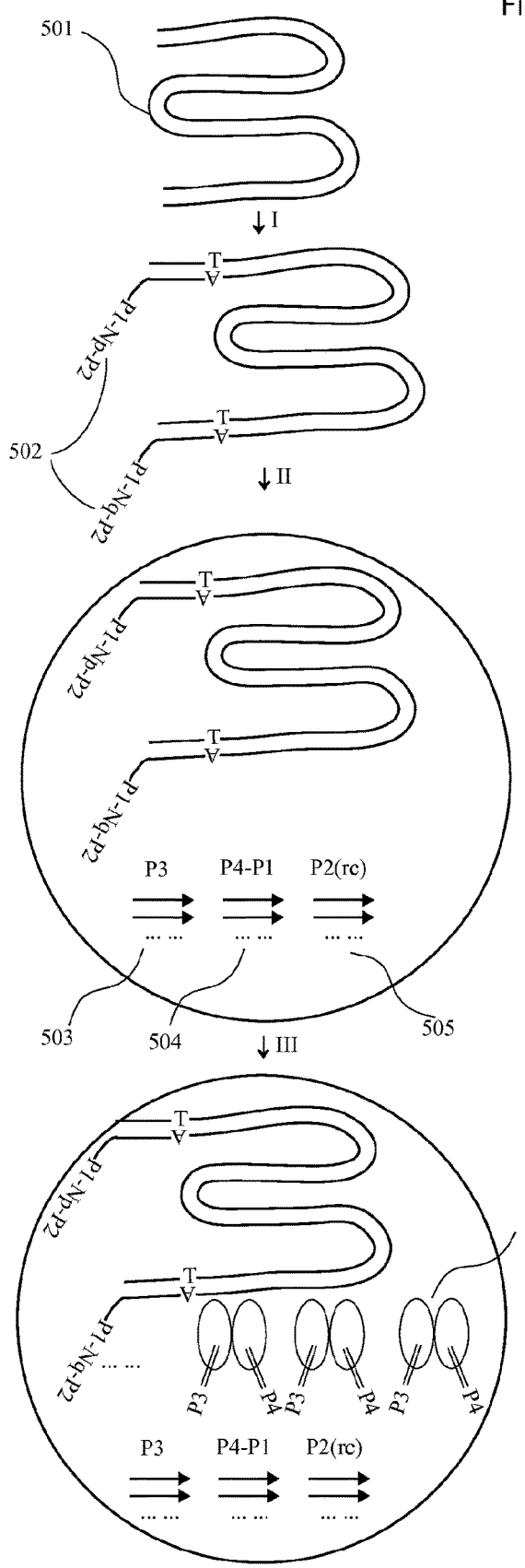
FIG. 5 illustrates another example of using the embodiment described in FIG. 3
Figure 5:
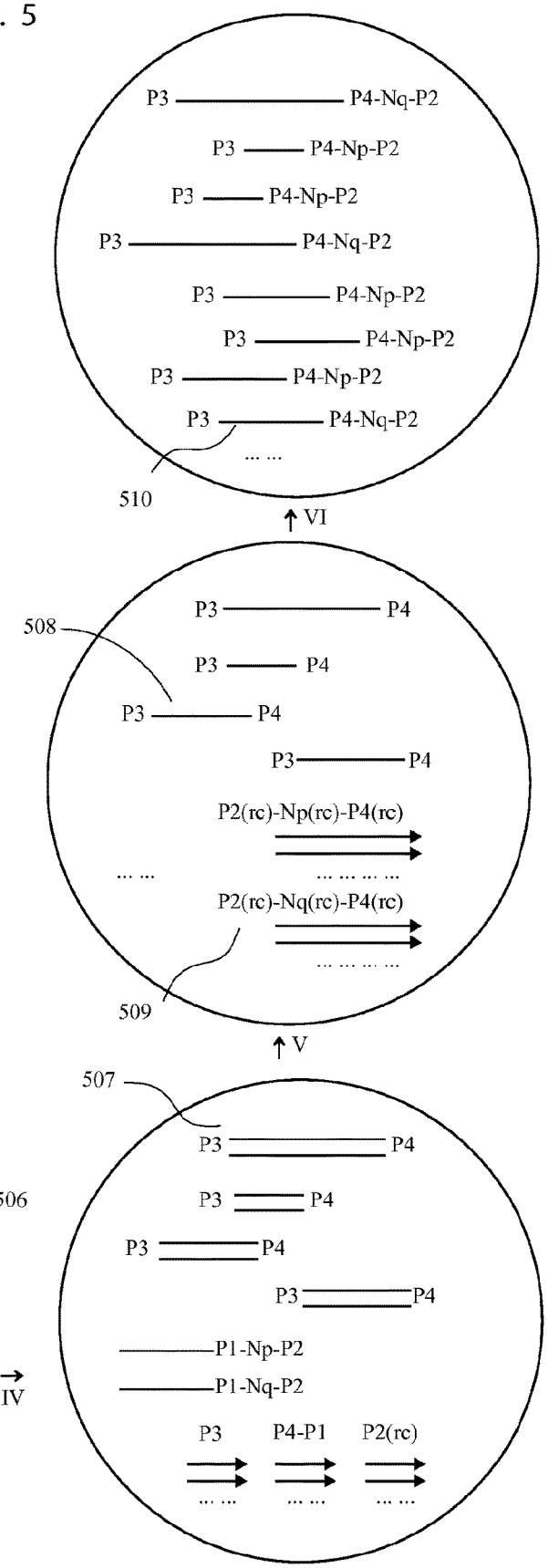

FIG. 5 illustrates an example of using the method of FIG. 3 to map the fragments of long DNA molecules.

I. A long DNA molecule (501) is end-repaired, dA-tailed and ligated with adapters on both ends. The 3' end (502) comprises a universal P1 sequence for primer binding, a UIS (Np or Nq). II. The long DNA molecule with the ligated adapters is put into droplet with PCR reagents comprising 3 different sets of primers, as P3 (503), P4-P1 (504), P2(rc) (505). III. Transpososome complexes with P3 and P4 adapter sequences are introduced into the droplets by droplet fusion or injection. IV. In the droplet, the long DNA molecule is fragmented by the transpososome complexes, and simultaneously P3, P4 are ligated to the ends of the DNA fragments, forming P3-genomic DNA-P4 constructs (507). V. Then a PCR reaction is initiated, in which the 3'end of the adapters (502) can be amplified by the primer P4-P1 and P2 (rc). By using excess of primer P2 (rc), the PCR products are dominantly single strand DNA (509) as P2 (rc)-Np (or Nq)-P4 (rc), whose 3'ends is complementary to P4. VI. After sufficient PCR cycles from V, the single strand PCR products and primer P3 can serve as primer pairs to amplify P3-genomic DNA-P4 (508) in the droplet, generating PCR products of P3-genomic DNA-P4-Np (or Nq)-P2. Finally, the PCR products from all the droplets can be pooled together and sequenced. By sorting the reads by the UIS, e.g. Np (or Nq), the genomic DNA sequence from the same long DNA can be mapped together.

Figure 6:
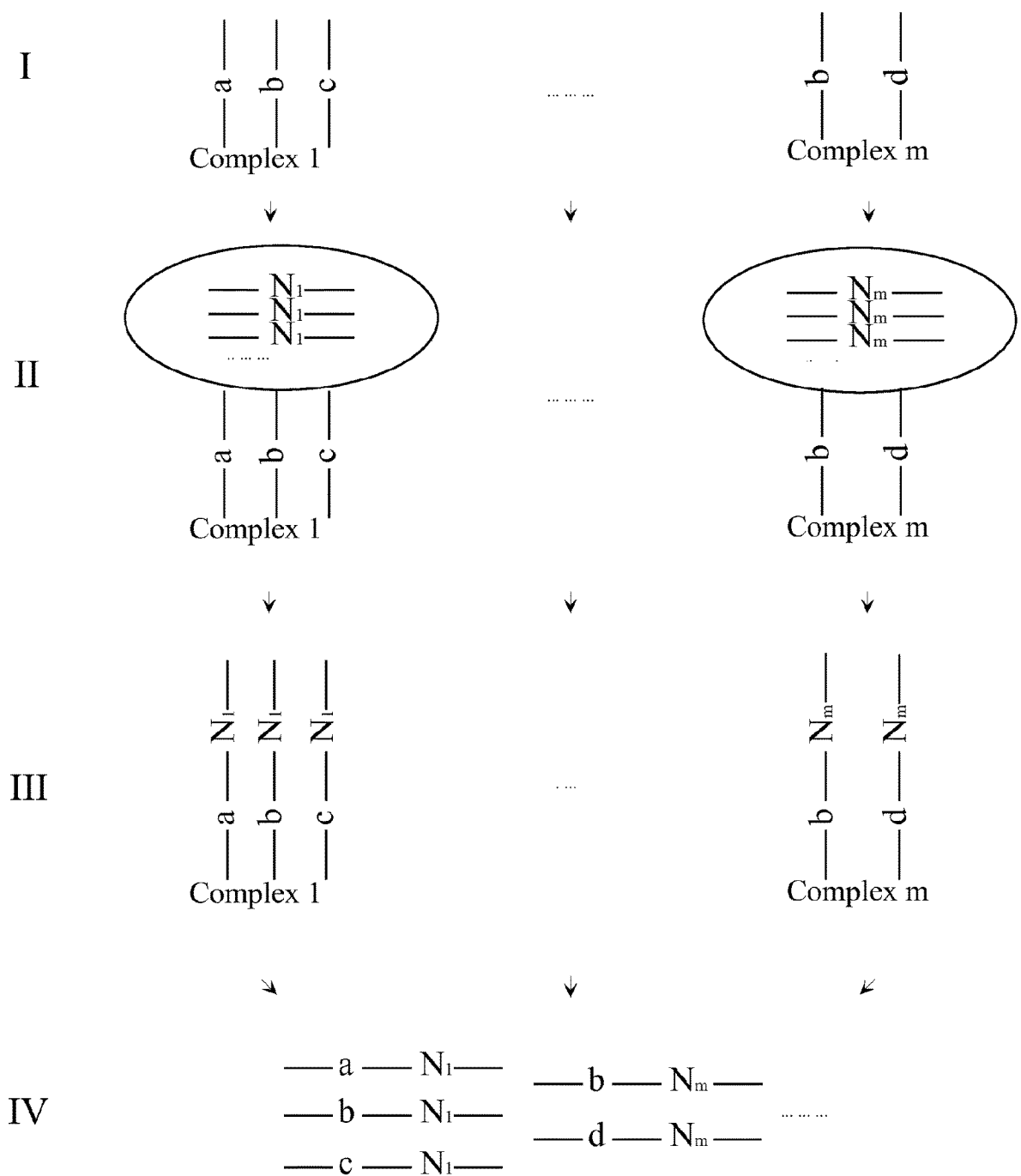
FIG. 6 is an illustration of a third embodiment of the invention.

FIG. 6 illustrates a method of labelling all the components of a complex with identical and unique tags by using clones of identical and unique tags attached to each complex I. The complexes to be analysed comprise complex constituents each such constituent containing a first UIS nucleic acid molecule sequence, e.g. DNA, RNA, or components that can be labelled with such an UIS nucleic acid molecule sequence, e.g. proteins that can be labelled by antibodies conjugated with a nucleic acid molecule sequence. Complex 1 comprises UISs a, b and c; complex m comprises UISs b and d. II. Then each complex is attached to a molecular construct. Each member of the set contains identical copies of a second UIS, e.g. a 15-mer of degenerate bases. The complex 1 is attached to a set comprising tag $N_1$ and complex m is attached to a set comprising tag $N_m$. III. Then the sets of unique tags are used to label all the nucleic acid sequences belonging to the respective complex, such that all the nucleic acid sequences of the same complex are labelled with identical and unique tags. For example, the a, b and c in complex 1 are all labelled with the unique tag $N_1$, and b and d in complex m are all labelled with the unique tag $N_m$. IV. Then all the labelled oligonucleotides are sequenced. Each sequencing read contains the first UIS, indicating the identity of the component, and also the second UIS indicating from which complex it originates. By sorting all the reads by the second UIS, and analyzing the coupled first UIS, all the components of each complex can be decoded.

Figure 7:
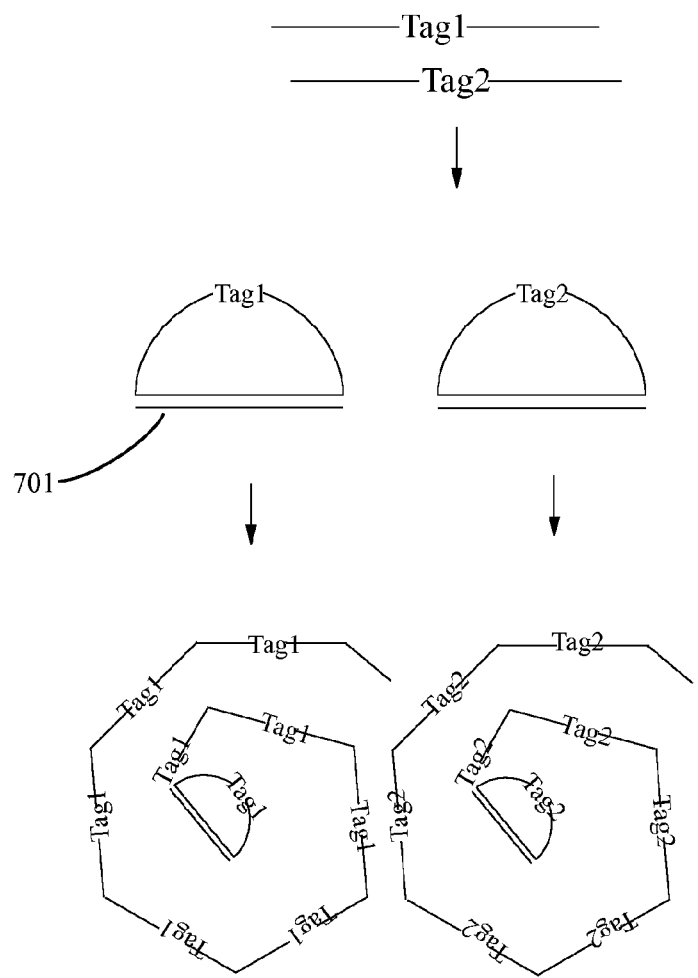
FIG. 7 illustrates an example of using the embodiment described in FIG. 6.

FIG. 7 illustrates an example of using nucleic acid constructs containing degenerate bases to make sets of unique tags in FIG. 6.

The tags containing a UIS, e.g. a degenerate 15-mer, and universal 5' and 3'ends can hybridize to another oligonucleotide (701) by its 5' and 3'-ends to be ligated into circular oligonucleotide. Then the circular oligonucleotide can be amplified by rolling circle amplification (RCA) to form DNA concatemers. Each DNA concatemer contains identical copies of the UIS. This DNA concatemer is a clone of a unique tag.

FIG. 8 illustrates an example of using the method of FIG. 6 to profile individual protein complexes.

I. In the two protein complexes illustrated, one consists of proteins A, B, and C, while the other one consists of proteins B and D. The protein complexes are probed by a set of molecular constructs comprising an antibody binding specifically to protein A, B, or C, respectively, conjugated with an oligonucleotide (801) containing an first UIS (a, b or c, respectively) and generic 3' end sequences (CTS). II. After removing the unbound conjugates, a second set of molecular construct tags is added, wherein the members of the second set of tags are DNA concatemers e.g. the RCA products from FIG. 7, with identical copies of an oligonucleotide (802), comprising a sequence complementary to the 3' end CTS of the first set of molecular construct tags (803) and a second UIS (804), a universal sequence as primer binding site (805), and another universal sequence as blocking oligo (807) binding site. The said DNA concatemers are allowed to hybridize on the 3'-end of the oligonucleotides of the molecular constructs, such that one DNA concatemer covers one protein complex. III. After removing the unbound DNA concatemers, a DNA polymerization is performed; making the nucleic acid molecules in the same complex obtain identical unique tags from the hybridized DNA concatemer, and also a universal sequence at the 3'end, which can be used as primer binding site. It's preferred that the extension products do not contain multiple unique tag sequences. This can be realized by using DNA polymerase with no strand displacement activity like *Sulfolobus* DNA Polymerase IV or T4 DNA polymerase together with blocking oligonucleotides (807) on the DNA concatemer to avoid excessive extension. IV. Then all extension the products are pooled and sequenced. The sequencing reads of a-tag 1, b-tag 1, and c-tag 1 would reveal one complex containing one protein A, one protein B and one protein C, while the reads of a-tag m, b-tag m would reveal another complex containing one protein A and one protein B.

Before pooling all the extension products. It's also feasible to obtain the second UIS of each DNA concatemer (e.g. tag1, tag2) directly from where it binds by in situ sequencing, for instance using sequencing by ligation. Then the UIS in each DNA concatemer will associate with a unique location or coordinates (e.g. tag1 with X1-Y1, tag2 with X2-Y2). After sequencing the extension products, the sequencing reads of a-tag1, b-tag1, and c-tag1 would reveal one complex containing one protein A, one protein B and one protein C, at the location of X1-Y1, while the reads of a-tag m, b-tag m would reveal another complex containing one protein A and one protein B at the location of X2-Y2).

An example of a detailed experimental protocol comprises:

Immobilizing the Antibody on a Solid Support

Antibody was first diluted into 1×PBS at the concentration of 1 ug/ml, then 20 µl of the antibody diluent was added to each reaction well of Roboscreen PCR strips, and incubated at 4° C. overnight. Then each reaction well was washed twice with 100 µl 1×PBS containing 0.05% T20 (PBST), then 50 µl 1×PBS containing 0.1% BSA (NEB) was added for blocking and preserving.

Preparing Antibody-Oligonucleotide Conjugate

Each antibody is conjugated with the oligonucleotide (one of oligo 7-21) as described in FIG. 4.

Preparing Streptavidin-Oligonucleotide Complex (STV-Oligos)

Streptavidin in 1×PBS (200 pM, 5 µl) was mixed with biotinylated oligonucleotides (4 nM, 5 µl) (one of oligo 23-26, or a mixture of oligo 23-26) and kept at 4° C. upon use.

Preparing DNA Concatemers Carrying Identical Copies of a Unique Tag

The padlock oligonucleotide (100 nM) (oligo 27) was first ligated into a circle on a template oligonucleotide (100 nM) (oligo 28) in 1×phi29 buffer (33 mM Tris-acetate (pH 7.9 at 37° C.), 10 mM Mg-acetate, 66 mM K-acetate, 0.1% (v/v) Tween 20, 1 mM DTT) with 1 mM ATP, 1 unit of T4 ligase in the volume of 100 ul. The ligation was performed on 37° C. for 30 minutes. Then 1 µl of 25 mM dNTP (dATP, dUTP, dCTP, dGTP) and 1 µl of phi29 polymerase (10 units/ul) were spiked into the ligation mix to initiate the rolling circle amplification (RCA) of the ligated circles. The RCA was performed at room temperature for 15 minutes and terminated by heating at 65° C. for 15 minutes.

Probing Protein Complexes Probed by Antibody-Oligonucleotide Conjugates

Protein complexes were diluted in 100 µl antibody diluent buffer (Olink) containing the antibody-oligonucleotide (10 nM for each), and incubated at 37° C. for 2 h.

Capturing Complexes Bound by Antibody-Oligonucleotides on Solid Support

The complexes were first diluted into 1×PBS with 0.1% BSA at a concentration below 1000 complexes per 1 ul. Then 10 µl of the complex diluent was added to the well with capturing antibodies, and incubated at RT for 30 minutes. Each reaction well was washed twice with PBST.

Barcoding Complexes

The DNA concatemers were diluted to a concentration of 1 nM in 1× ThermoPol Reaction Buffer (2 mM Tris-HCl, 1 mM $(NH4)_2SO_4$, 1 mM KCl, 0.2 mM $MgSO_4$, 0.01% Triton® X-100) containing 200 nM blocking oligonucleotides (Oligo 62). 10 µl of the DNA concatemer was added to each well containing the captured complex to allow the DNA concatermer to hybridize on the captured complex. The hybridization was performed at 37° C. for 15 minutes, followed by washing twice with 100 µl PBST for each reaction well. Then 10 µl of 1× ThermoPol Reaction Buffer (NEB) containing 250 µM dNTP (dATP, dTTP, dGTP, dCTP), 1 unit of *Sulfolobus* DNA Polymerase IV (NEB) to initiate the DNA extension. The extension was performed at 37° C. for 15 minutes, followed by washing twice with 100 µl PBST for each reaction well.

Amplifying Extension Products.

1×PCR buffer of 50 ul, containing 100 nM forward (oligo 3) and 100 nM reverse primer (oligo 29), 200 µM dNTP (dATP,dUTP,dGTP,dCTP), 1.5 units Taq polymerase, 1 unit Uracil-DNA Glycosylase (Thermal Scientific) was added to each reaction well, and incubated at 37° C. for 30 minutes to cleave the DNA concatemers and circles containing Uracil bases. Then a PCR reaction was performed as 95° C. 2 min, followed by 40 cycles of 95° C., 15 seconds, 60° C. 1 min.

Introducing Sequencing Adapters and Sample Barcodes

One µl water containing a pair of primers (5 µM each) (one of oligo 30-37, and one of oligo 38-45) was spiked into each PCR mixture, followed by 2 cycles of 95° C., 15 seconds and 60° C. 1 minute and 1 cycle of 70° C. for 7 minutes. Then 1 µl of the PCR mixture was taken from each PCR mixture and added to a new well containing 50 µl of PCR mixture containing 100 nM forward (oligo 46) and 100 nM reverse primer (oligo 47), 200 µM dNTP (dATP,dUTP, dGTP,dCTP), 1.5 units Plantinum Taq polymerase. Then PCR reaction was performed as 20 cycles of (95° C., 15 seconds, 60° C. 1 minute). Then an extra cycle was performed after spiking in 1 µl of primer pairs (10 µM) (oligo 46 and 47), to make the PCR products fully double stranded. Then the products sequenced by next generation sequencing (NGS), e.g. IonTorrent, Illumina.

Figure 9:
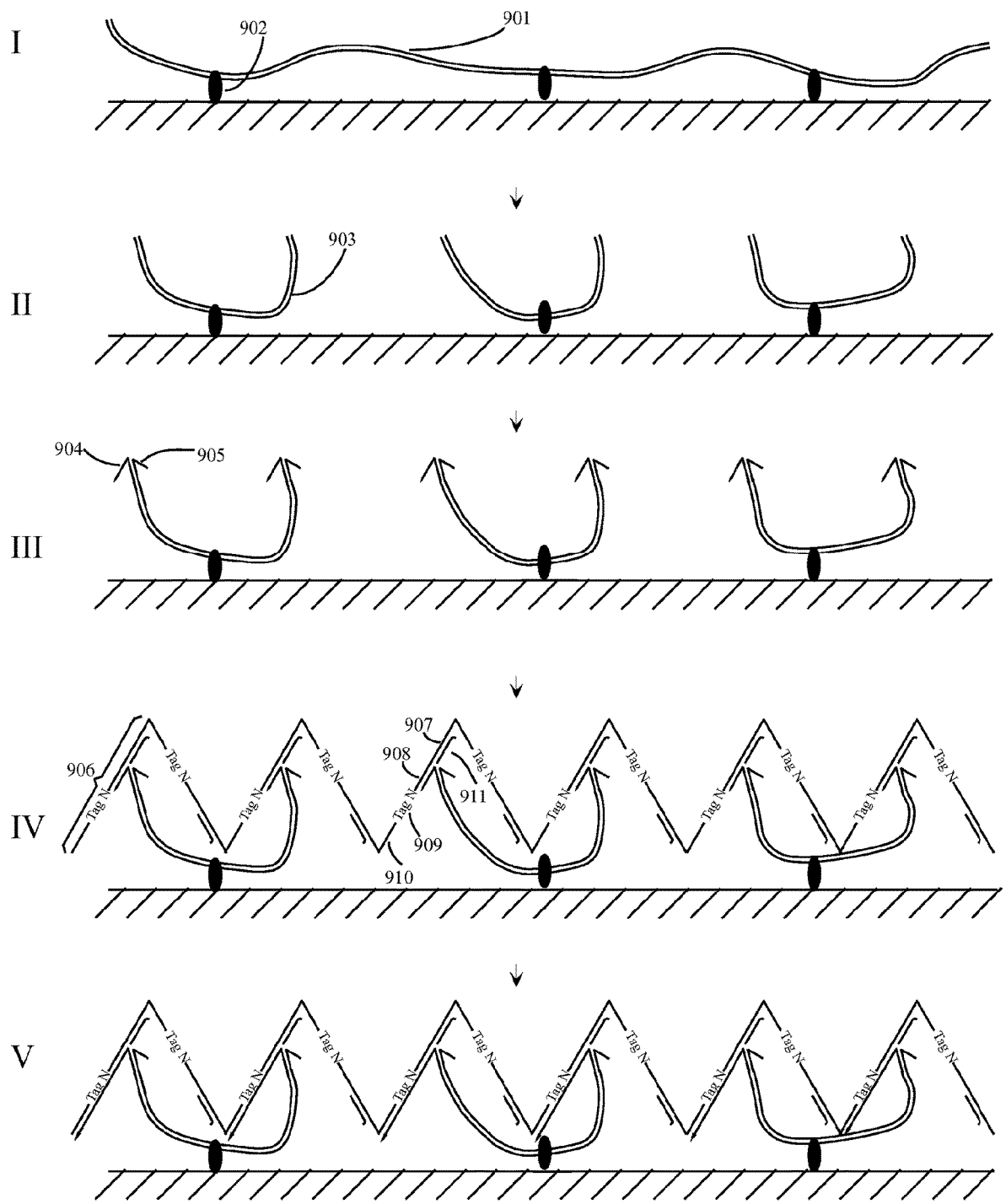
FIG. 9 illustrates a third example of the embodiment described in FIG. 6.

FIG. 9 illustrates an example of using the method of FIG. 6 to map long DNA molecules.

I. A long DNA molecule (901) is immobilized on surface by covalent crosslinking or using antibody against common DNA binding proteins e.g. histones (902). II. The long DNA molecule is fragmented, and the fragments (903) still remain in proximity. III. Then all the fragments are ligated with a common adapter on both end, with universal 5'end (905) and 3'end (904). IV. Then DNA concatemers (e.g. from RCA reaction in FIG. 7) of identical copies of a unit (906), comprising a sequence (908) complementary to the 3'end of the adapter, a UIS (909), a primer binding site (910), and another primer binding site for a blocking oligo (911). The said DNA concatemers are allowed to hybridize on the 3'-end of the oligonucleotides of the molecular constructs, such that each DNA concatemer preferably covers the DNA fragments from the same original long DNA molecule. V. Then a DNA polymerization reaction is carried out as in FIG. 8, to make each DNA fragment from the same long DNA molecule obtain the identical UIS from the same DNA concatemer. Then the products are pooled and sequenced by NGS. By sorting the reads with UIS, the sequences from the same long DNA can be obtained.

Figure 10:
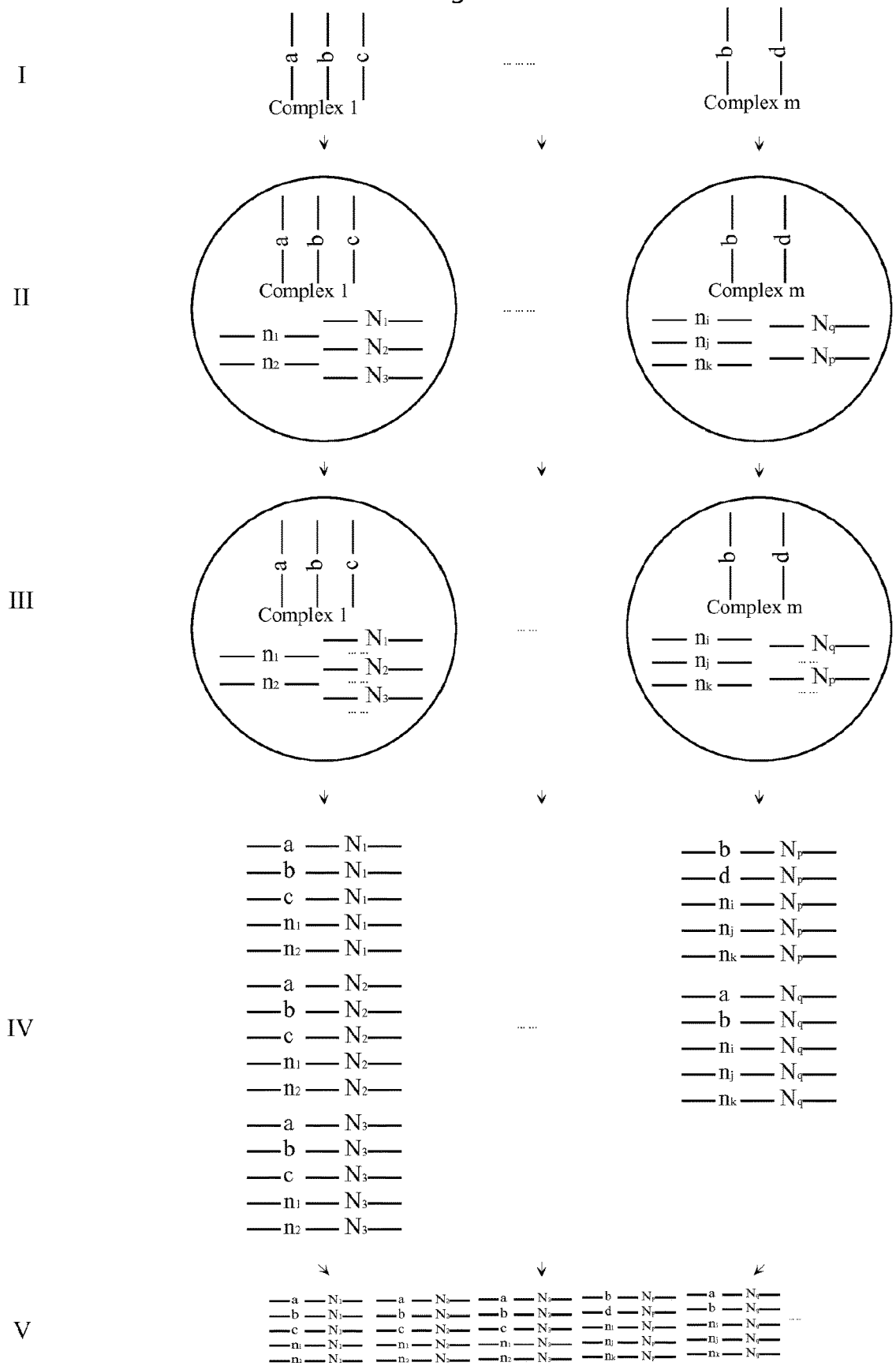
FIG. 10 is an illustration of a fourth embodiment of the invention.

FIG. 10 illustrates a method of labelling all the components of a complex with the same set of identical and unique tags.

I. The complexes to be analysed comprise complex constituents each such constituent containing a first UIS nucleic acid molecule sequence, e.g. DNA, RNA, or components that can be labelled with such an UIS nucleic acid molecule sequence, e.g. proteins that can be labelled by antibodies conjugated with a nucleic acid molecule sequence. Complex 1 comprises UISs a, b and c; complex m comprises UISs b and d. II. Then the complexes are put into a PCR mix containing two sets of tags. Members of both of the two sets contain a piece (e.g. 15-mers) of degenerate bases as a UIS, set 1 with a second UIS as $n_1, n_2 \ldots n_i, n_j, n_k \ldots$ and set 2 with a third UIS as $N_1, N_2, N_3 \ldots N_p, N_q$. Then the complexes together with the two sets of tags are put into droplets, such that each droplet contains 0 or 1 complex, and a random number of members of set 1 and set 2 tags. For example in the droplet containing complex1, there are two members of set 1 as $n_1, n_2$, and three members of set 2 as $N_1, N_2, N_3$, and in the droplet containing complex m, there are three members of set 1 as $n_j, n_k$ and two members of set 2 as $N_p, N_q$. III. Then the members of set 2 in each droplet are amplified by emulsion PCR by forward and reverse primers. After sufficient PCR cycles, and by using excess of the reverse primer, the amplified products are dominated by single strand DNA products, which can serve as primers to extend on the nucleic acid part of the molecular construct tags on the complex and also the set 1 tags in each droplet. This can be achieved by, for instance, designing the 3'-end of the oligonucleotides of the members of set 1 to have the same sequence as the 5'-overhang sequence of forward primer. IV. Finally all the first and second UIS in each droplet are labelled with the members of set 2 tags. As illustrated, in the droplet containing complex1, all the nucleic acids and members of set 1 (a, b, c, $n_1, n_2$) are labelled with $N_1, N_2$, and $N_3$, and in the droplet containing the complex m, all the nucleic acids and members of set 1 (b, d, $n_i, n_j, n_k$) are labelled with $N_p$ and $N_q$. V. Then all the droplets are destroyed and the DNA molecules are pooled and sequenced. By analysing the second UIS from set 1 and the coupled third UIS, the composition of members of set 2 in each droplet can be decoded. For example the reads of $n_1$-$N_1$, $n_1$-$N_2$, $n_1$-$N_3$, would indicate $N_1, N_2, N_3$ are in one droplet. Then using the reads containing $N_1$, or $N_2$, or $N_3$, for example the reads of a-$N_1$, b-$N_2$, c-$N_3$ would indicate identity oligonucleotide (the first UIS) a, b and c are in the same the droplet (or on complex it contained). Therefore by sorting the reads by set 1 and set 2 tags, the nucleic acid part of the molecular construct tags on each complex can be decoded.

FIG. 11 illustrates an example of using the method of FIG. 8 to quantify several proteins on single cells.

I. One cell has one protein A, one protein B and one protein C, and another cell has one protein B and one protein D. The proteins on each cell are probed by a first set of molecular construct tags comprising an antibody binding specifically to the respective proteins and being conjugated with a oligonucleotide (1101), each comprising a universal sequence P1 for primer binding, a first UIS (a, b, c, or d) corresponding to the protein for which the antibody is specific, and another universal sequence P4 for primer binding. II. Then each cell with the bound antibody-oligonucleotides are diluted into the PCR mix containing two sets of tags (set 1 (1102) and set 2 (1103) tag, and then put into droplets (e.g. water in oil emulsions), such that one droplet contains 0 or 1 cell and a random number of set 1 and set 2 tags. For example in one droplet containing a cell, there are two set 1 tags and three set 2 tags, while in another droplet containing a cell, there are three set 1 tags and two set 2 tags. Both the set 1 and set 2 tags contain a piece (e.g. 15mers) of degenerate bases as an UIS, set 1 with a second UIS as $n_1, n_2 \ldots n_i, n_j, n_k$ and set 2 with a third UIS as $N_1, N_2, N_3 \ldots N_p, N_q$. The tags further comprise two CTSs, serving as primers. These are denoted P1 and P4 for set 1 and P2 and P3 for set 2 in the figure. In the droplet, the additional primers P4-P2 (1105) and P3 (rc) (1106) can amplify the set 2 oligonucleotides in each droplet. It's feasible to make the oligonucleotides on the antibodies to carry the set 1 or set 2 tags. By doing so, the droplets without cells, there are no set 1 or set 2 tags. It's also feasible to dilute localized amplification products of set 2 tags e.g. by rolling circle amplification to the droplets. By doing so, each droplet would contain several clones of set 2 tags. III. After sufficient PCR cycles, by using excess of primer P3 (rc), the amplified products in each droplet are single strand DNA as P3(rc)-N-P2(rc)-P4(rc), containing a universal 5'-end P3, a third UIS, and a universal 3'-end P4(rc), which with another primer P1 (1104) in the droplet can amplify the set 1 tags and also the first set of molecular construct tags (1101) in the following PCR cycles. IV. Finally the set 1 tags (comprising the second UIS) and the first set of molecular construct tags (comprising the first UIS) are all labelled by the same set of set 2 tags (comprising the third UIS) in each droplet. Then all the droplets can be destroyed and the DNA molecules are pooled and sequenced. By sorting the sequencing reads using the second UIS and the couple third UIS, the composition of set 2 tags in each droplet can be identified. And then sorting all the reads by using the third UIS, and the coupled first UIS, the composition of first set of molecular construct tags (respective to each protein) in each droplet (on each cell) can be decoded.

A detailed experimental protocol comprises:

Preparing Antibody-Oligonucleotide Conjugate

Each antibody is conjugated with the oligonucleotide (one of oligo 7-21) as described in FIG. 4.

Probe Binding

The cells in suspension were washed by twice by PBST. After removing the washing buffer, 500 µl antibody dilution buffer containing probes, each at the concentration of 1 nM, was added to the cells and incubated at room temperature on a rotator for 2 hours. The cells were washed three times with 1×PBST.

Emulsion PCR

After removing the PBST, the cells were diluted to the concentration of around 10 cells/µl in 200 µl 1×ddPCR Supermix for Probes (Bio-rad) containing 100 nM forward primer1 (oligo 3), 25 nM forward primer 2 (oligo 59), and 100 nM reverse primer (oligo 6), 1 fM set 1 tags (oligo 60), 1 fM set 2 tags (oligo 61). Then the mixture was transferred to the well for samples of DG8 cartridge (Bio-rad). Then 70 µl droplet generating oil was added to each of the well for oil in the cartridge. Then the cartridge was placed on QX100 droplet generator (Bio-Rad). Then the droplets were transferred to a 96-well PCR plate, and put on a thermal cycler at the program 95° C. 10 minutes, 60 cycles of 95° C. for 30 s, 60° C. for 1 minute. Then the droplets were destroyed and the PCR products were extracted.

Sequencing

The collected PCR products were purified and sequenced by next generation sequencing (NGS), e.g. Miseq, Hiseq 2500, Ion torrent.

Figure 12:
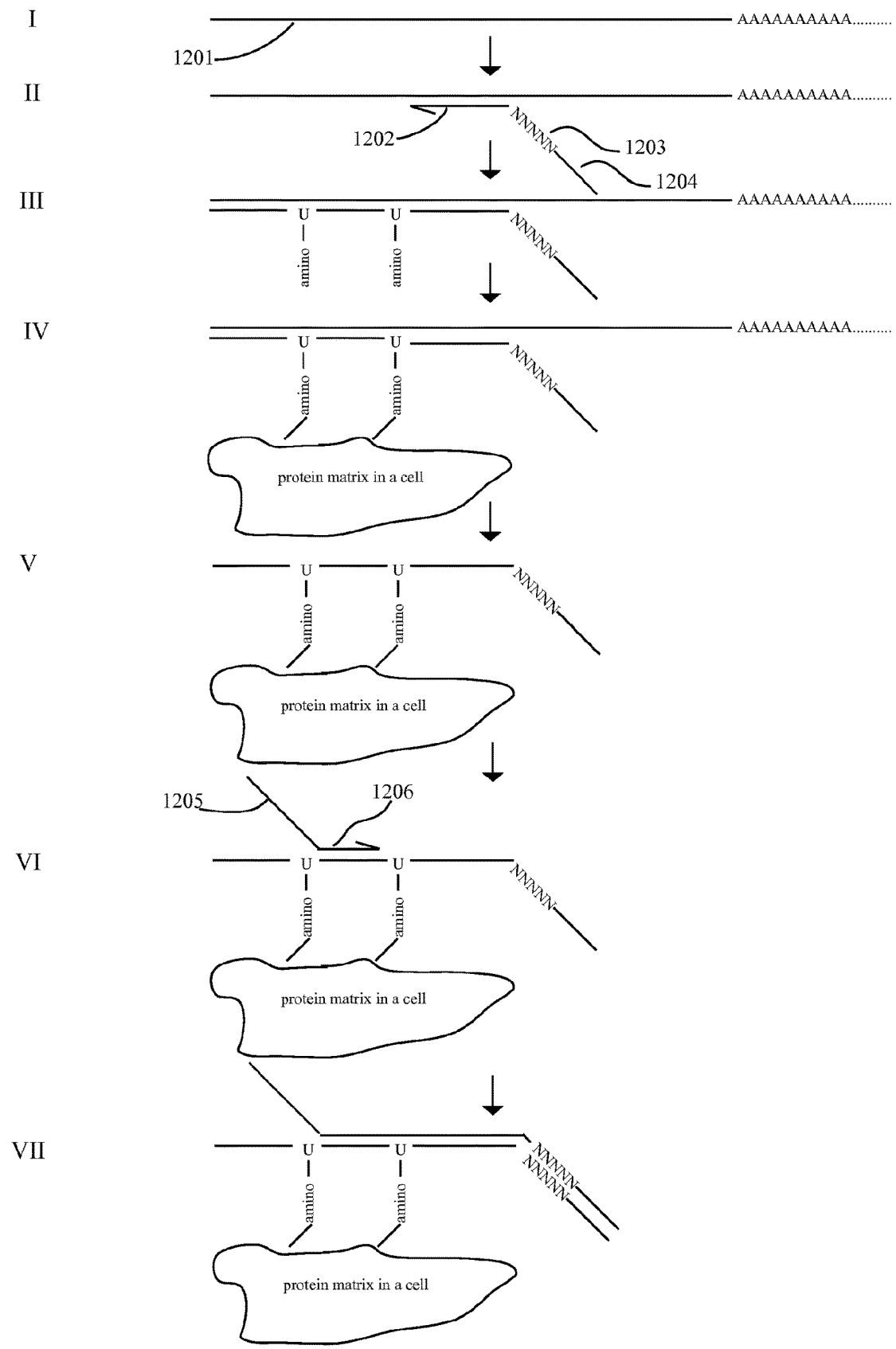
FIG. 12 illustrates another example of using the embodiment described in FIG. 10.

FIG. 12 illustrates an example of using the method of FIG. 10 to count RNA molecules on single cells.

I. The mRNA molecule in each cell (1201) is first fixed on the cell. II. Then cDNA primers comprising a universal sequence at the 5'end (1204), a UIS (1203) and a RNA specific sequence (1202) are allowed to bind on the RNA molecules. III. cDNA is synthesised on cells by using reverse transcriptase. In the reaction, dUTP with amine group is used together with normal dUTP, so that the cDNA contains amine group. IV. The cDNA is cross-linked to the cells by its amine groups to other amine groups in the cells, e.g. from proteins. V. Then the RNA is removed by using RNase H. VI. Then a DNA primer comprising a universal 5'end (1205) and sequence specific primer at the 3'end (1206) is allowed to hybridize on the cDNA. VII. A DNA polymerization reaction is carried out, generating a DNA molecule comprising a universal 5' end sequence, cDNA sequence, a UIS, and a universal 3'end. Then the cells with the bound products can be put into droplets, followed by emulsion PCR for barcoding, in the similar procedure as FIG. 11. After sequencing and soring the reads, the sequencing reads from the same cell can be put together. The absolute number molecules for each RNA can be obtained using the UIS (1203) together with the associated cDNA sequence in the same read.

By using specific cDNA primers to a certain types of RNA molecules can greatly save the sequencing reads for each cell. But it would be feasible to use unspecific cDNA primer, e.g. oligo dT primers, degenerate bases at 3'end to synthesize cDNA of all RNA molecules and introduce the 3'end universal sequence by strand switch reaction by the reverse transcriptase.

Figure 13:
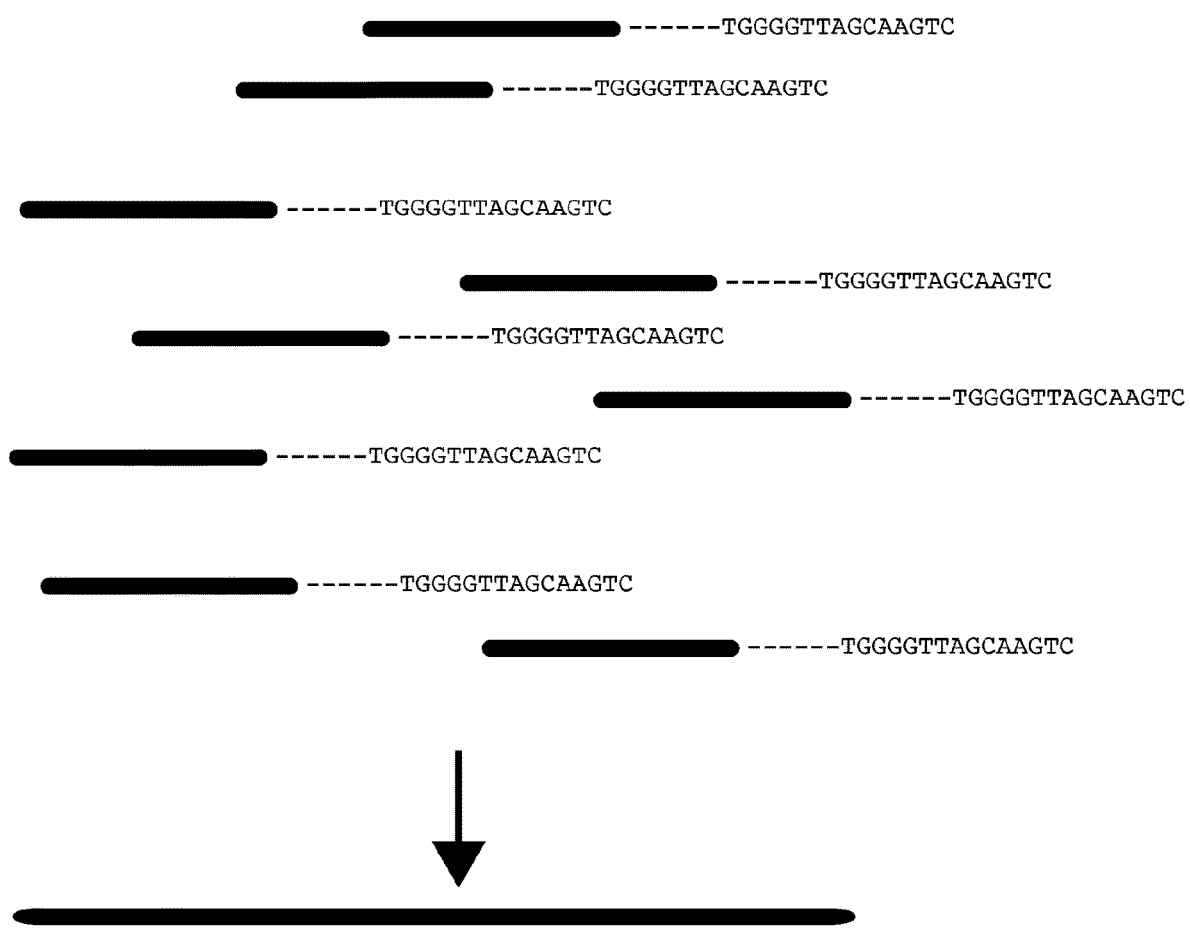
FIG. 13 illustrates the result from FIG. 2.

FIG. 13 illustrates a hypothetical result from FIG. 2.

The sequencing reads were sorted based on the UIS of the molecular construct tag. One UIS is 'TGGGGTTAG-CAAGTC' (SEQ ID NO: 63), and the reads sharing this sequence at their 3'-ends are put together and their 5'-end reads were mapped to obtain the long DNA fragment sequence.

Figure 14:
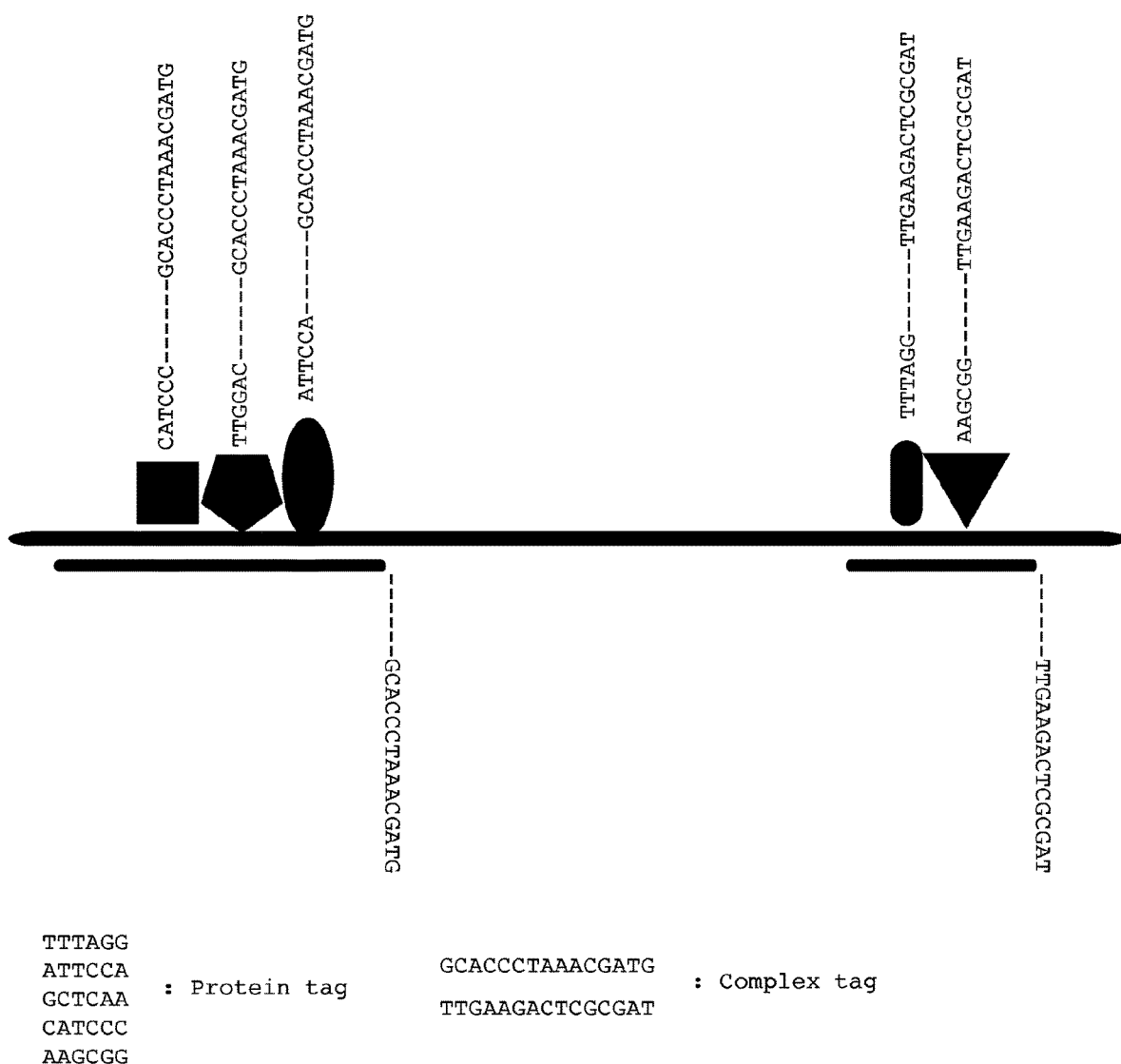
FIG. 14 illustrates the result from FIG. 4.

FIG. 14 illustrates a hypothetical result of an experiment according to the method of FIG. 4.

The UISs a, b, c, d, and e are given as TTTAGG, ATTCCA, GCTCAA, CATCCC, and AAGCGG. The sequencing reads were sorted based on the UIS $N_1$ or $N_m$, given as GCACCCTAAACGATG (SEQ ID NO: 64) and TTGAAGACTCGCGAT (SEQ ID NO: 65), respectively. Then the protein tags (a, b, c, d or e) and the genomic sequences sharing the same UIS $N_1$ or $N_m$, can be mapped together to the genome.

Figure 15:
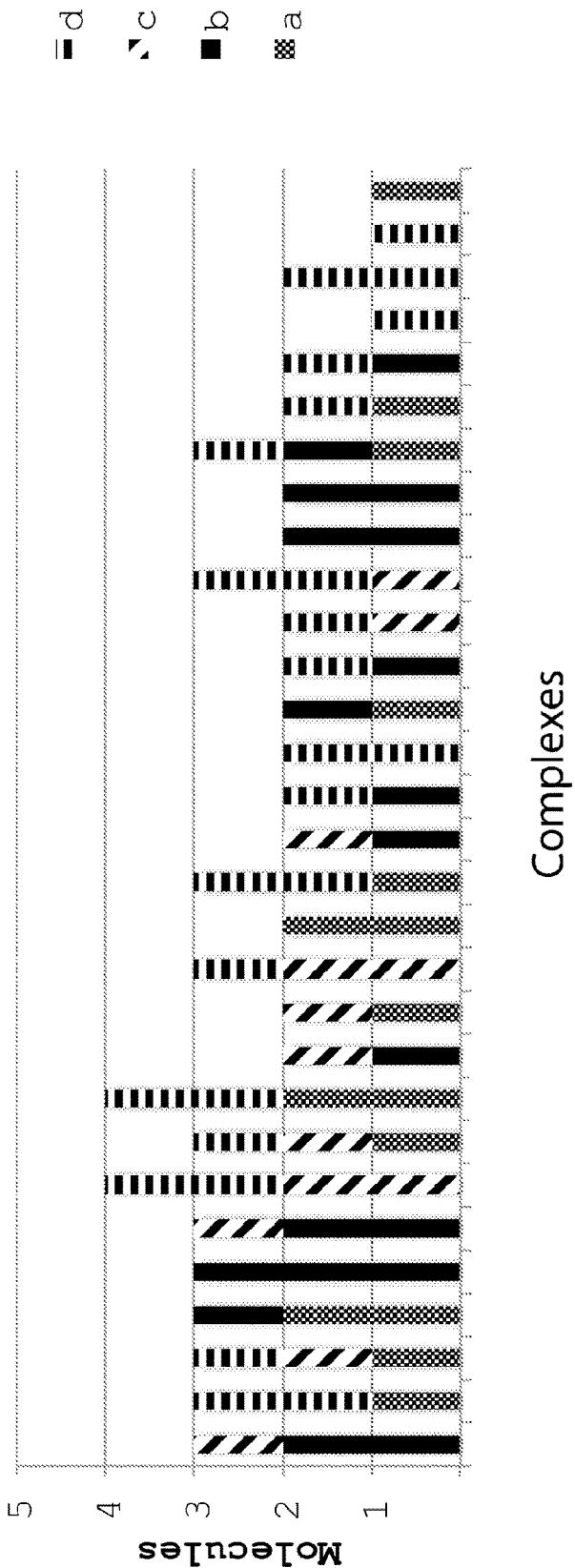
FIG. 15 illustrates the result from FIG. 8.

FIG. 15 illustrates a result from a method according to FIG. 8.

To mimic a protein complex, streptavidin was incubated with a mixture of 4 different molecular construct tags consisting of biotinylated oligonucleotide tags with UISs a, b, c and d. That is, biotin was used to mimic an antibody binding specific to a protein which in this case was mimicked by streptavidin. Then streptavidin-oligonucleotides complexes were profiled by the method described in FIG. 8. After sequencing, the reads sharing the same tags of the second set, as shown on the x-bar, were put together, By using the UIS of the first set of tags on biotinylated oligonuceotides, the absolute number of oligonucleotides on each streptavidin can be counted. The result showed each streptavidin was bound by a random combination of 4 different biotinylated oligonucleotides. Since the streptavidin can form tetramer, it can bind a maximum of 4 biotinylated oligonucleotides, which was consistent with the experimental preparation.

FIG. 16 illustrates a further result from a method according to FIG. 8.

Similar as FIG. 15, but the streptavidin was incubated with only one type of biotinylated oligonucleotides then mixed and profiled by the method described in FIG. 8. After sequencing, the reads sharing the same unique tags were put together. By using another random barcode of biotinylated oligonucleotides, the absolute number of oligonucleotides on each streptavidin can be counted. The results showed each streptavidin contains only one type of biotinylated oligonucleotide, which was consistent with the experimental preparation.

FIG. 17 illustrates a result from a method according to FIG. 11.

To mimic antibody-oligonucleotides conjugates binding on cells. Streptavidin coated magnetic beads were incubated with different concentration (d<c<b<a) of biotinylated oligonucleotides as set 1 tags (in FIG. 9). The four different prepared beads were diluted in PCR mix with same concentration of set 2 tags. In the beginning PCR circles, the set 2 tags were amplified, and the amplification curves of the 4 reactions gave a similar Ct (Cycle threshold). In the following PCR circles, a second phase of PCR were initiated to amplify the set 1 tags, in which the curves of the four reactions gave a different Ct values, which was consistent with the concentration of set 1 tags.

When practicing the present invention the person skilled in the art may further make of use conventional techniques in the field of pharmaceutical chemistry, immunology, molecular biology, microbiology, cell biology, transgenic animals and recombinant DNA technology, as i.a. disclosed in Sambrook et al. "Molecular cloning: A laboratory manual", 3$^{rd}$ ed. 2001; Ausubel et al. "Short protocols in molecular biology", 5$^{th}$ ed. 1995; "Methods in enzymology", Academic Press, Inc.; MacPherson, Hames and Taylor (eds.). "PCR 2: A practical approach", 1995; "Harlow and Lane (eds.) "Antibodies, a laboratory manual" 1988; Freshney (ed.) "Culture of animal cells", 4$^{th}$ ed. 2000; Hogan et al. "Manipulating the Mouse Embryo: A Laboratory Manual", Cold Spring Harbor Laboratory, 1994; or later editions of these books, and Ke R, Mignardi M, Pacureanu A, et al. In situ sequencing for RNA analysis in preserved tissue and cells. *Nat Methods* 2013; 10:857-60, and Lee J H, Daugharthy E R, Scheiman J, et al. Highly multiplexed subcellular RNA sequencing in situ. Science 2014; 343: 1360-3.

The present invention is not limited to the above-described preferred embodiments. Various alternatives, modifications and equivalents may be used. Therefore, the above embodiments should not be taken as limiting the scope of the invention, which is defined by the appending claims.

TABLE 1

| Name | 5' modification | Sequence | 3' modification | SEQ ID NO |
|---|---|---|---|---|
| oligo 1 | | GCGAAACCTGGTCCGGTATC NNNNNNNNNNNNNNNNGATG TTGAAGGCA | | 1 |
| oligo 2 | phosphorylation | GCCTTCAACATCTTGCGTGT GATTCCTAGTAATG | | 2 |
| oligo 3 | | GCGAAACCTGGTCCGGTATC | | 3 |
| oligo 4 | | CATTACTAGGAATCACACGC | | 4 |
| oligo 5 | | TACCTCTATTGATACGTGGG NNNNNN | | 5 |
| oligo 6 | | TACCTCTATTGATACGTGGG | | 6 |
| oligo 7 | Azide | GCGAAACCTGGTCCGGTATC TTTAGGNNNNNNNNNNTGCT ATTATGATGTCTCAGGT | | 7 |
| oligo 8 | Azide | GCGAAACCTGGTCCGGTATC ATTCCANNNNNNNNNTGCT ATTATGATGTCTCAGGT | | 8 |
| oligo 9 | Azide | GCGAAACCTGGTCCGGTATC GCTCAANNNNNNNNNTGC TATTATGATGTCTCAGGT | | 9 |
| oligo 10 | Azide | GCGAAACCTGGTCCGGTATC CATCCCNNNNNNNNNTGCT ATTATGATGTCTCAGGT | | 10 |

TABLE 1-continued

| Name | 5' modification | Sequence | 3' modification | SEQ ID NO |
|---|---|---|---|---|
| oligo 11 | Azide | GCGAAACCTGGTCCGGTATC AAGCGGNNNNNNNNNNTGC TATTATGATGTCTCAGGT | | 11 |
| oligo 12 | Azide | GCGAAACCTGGTCCGGTATC AATAAANNNNNNNNNNTGC TATTATGATGTCTCAGGT | | 12 |
| oligo 13 | Azide | GCGAAACCTGGTCCGGTATC GAGGAGNNNNNNNNNNTGC TATTATGATGTCTCAGGT | | 13 |
| oligo 14 | Azide | GCGAAACCTGGTCCGGTATC GGTACANNNNNNNNNNTGC TATTATGATGTCTCAGGT | | 14 |
| oligo 15 | Azide | GCGAAACCTGGTCCGGTATC AGCGAGNNNNNNNNNNTGC TATTATGATGTCTCAGGT | | 15 |
| oligo 16 | Azide | GCGAAACCTGGTCCGGTATC GTCGGTNNNNNNNNNNTGC TATTATGATGTCTCAGGT | | 16 |
| oligo 17 | Azide | GCGAAACCTGGTCCGGTATC ATTTGCNNNNNNNNNNTGCT ATTATGATGTCTCAGGT | | 17 |
| oligo 18 | Azide | GCGAAACCTGGTCCGGTATC AGGACTNNNNNNNNNNTGC TATTATGATGTCTCAGGT | | 18 |
| oligo 19 | Azide | GCGAAACCTGGTCCGGTATC AGGACTNNNNNNNNNNTGC TATTATGATGTCTCAGGT | | 19 |
| oligo 20 | Azide | GCGAAACCTGGTCCGGTATC TCGTAANNNNNNNNNNTGC TATTATGATGTCTCAGGT | | 20 |
| oligo 21 | Azide | GCGAAACCTGGTCCGGTATC CCAGACNNNNNNNNNNTGC TATTATGATGTCTCAGGT | | 21 |
| oligo 22 | Azide | CTCTCTCTCTCTCTCTCT CTCTCTCTCT | biotin | 22 |
| oligo 23 | biotin | GCGAAACCTGGTCCGGTATC TTGGACNNNNNNNNNNTGC TATTATGATGTCTCAGGT | | 23 |
| oligo 24 | biotin | GCGAAACCTGGTCCGGTATC CTGTGTNNNNNNNNNNTGCT ATTATGATGTCTCAGGT | | 24 |
| oligo 25 | biotin | GCGAAACCTGGTCCGGTATC GGACATNNNNNNNNNNTGC TATTATGATGTCTCAGGT | | 25 |
| oligo 26 | biotin | GCGAAACCTGGTCCGGTATC CAAAGTNNNNNNNNNNTGC TATTATGATGTCTCAGGT | | 26 |
| oligo 27 | phosphorylation | GCTATTATGATGTCTCAGGT AANNNNNNNNNNNNNNNTT TCCCACGTATCAATAGAGGT AGCAGTCACGTTCTCGAATC GCTAGTGCTGGATGATCGTC C | | 27 |
| oligo 28 | | CTGAGACATCATAATAGCGG ACGATCATCCAGCACT | | 28 |
| oligo 29 | | CGATTCGAGAACGTGACTGC | | 29 |

TABLE 1-continued

| Name | 5' modification | Sequence | 3' modification | SEQ ID NO |
|---|---|---|---|---|
| oligo 30 | | CCATCTCATCCCTGCGTGTCTCCGACTCAGGGTTTGGCGAAACCTGGTCCGGTATC | | 30 |
| oligo 31 | | CCATCTCATCCCTGCGTGTCTCCGACTCAATGGCGGGCGAAACCTGGTCCGGTATC | | 31 |
| oligo 32 | | CCATCTCATCCCTGCGTGTCTCCGACTCATTCATAGGCGAAACCTGGTCCGGTATC | | 32 |
| oligo 33 | | CCATCTCATCCCTGCGTGTCTCCGACTCAAACGCCGGCGAAACCTGGTCCGGTATC | | 33 |
| oligo 34 | | CCATCTCATCCCTGCGTGTCTCCGACTCAGGCTGCGGCGAAACCTGGTCCGGTATC | | 34 |
| oligo 35 | | CCATCTCATCCCTGCGTGTCTCCGACTCAGGCTGCGGCGAAACCTGGTCCGGTATC | | 35 |
| oligo 36 | | CCATCTCATCCCTGCGTGTCTCCGACTCAAGATGGGCGAAACCTGGTCCGGTATC | | 36 |
| oligo 37 | | CCATCTCATCCCTGCGTGTCTCCGACTCAGTAATGGGCGAAACCTGGTCCGGTATC | | 37 |
| oligo 38 | | CCTCTCTATGGGCAGTCGGTGATCATGATTACCTCTATTGATACGTGGG | | 38 |
| oligo 39 | | CCTCTCTATGGGCAGTCGGTGATTGTGCGTACCTCTATTGATACGTGGG | | 39 |
| oligo 40 | | CCTCTCTATGGGCAGTCGGTGATGCAGGATACCTCTATTGATACGTGGG | | 40 |
| oligo 41 | | CCTCTCTATGGGCAGTCGGTGATTCTACCTACCTCTATTGATACGTGGG | | 41 |
| oligo 42 | | CCTCTCTATGGGCAGTCGGTGATAGTCGTTACCTCTATTGATACGTGGG | | 42 |
| oligo 43 | | CCTCTCTATGGGCAGTCGGTGATCGTGGCTACCTCTATTGATACGTGGG | | 43 |
| oligo 44 | | CCTCTCTATGGGCAGTCGGTGATGCGTCCTACCTCTATTGATACGTGGG | | 44 |
| oligo 45 | | CCTCTCTATGGGCAGTCGGTGATGAACGCTACCTCTATTGATACGTGGG | | 45 |
| oligo 46 | | CCATCTCATCCCTGCGTGTCTCCGACTCAG | | 46 |
| oligo 47 | | CCTCTCTATGGGCAGTCGGTGAT | | 47 |
| oligo 48 | Azide | AACGATTCGAGAACGTGACTGCNNNNNNNNNNNNTTTAGGTCCCACGTATCAATAGAGGTA | | 48 |
| oligo 49 | Azide | AACGATTCGAGAACGTGACTGCNNNNNNNNNNNNATTCCATCCCACGTATCAATAGAGGTA | | 49 |
| oligo 50 | Azide | AACGATTCGAGAACGTGACTGCNNNNNNNNNNNNGCTCAATCCCACGTATCAATAGAGGTA | | 50 |
| oligo 51 | Azide | AACGATTCGAGAACGTGACTGCNNNNNNNNNNNNCATCCCTCCCACGTATCAATAGAGGTA | | 51 |
| oligo 52 | Azide | AACGATTCGAGAACGTGACTGCNNNNNNNNNNNNTTGGACTCCCACGTATCAATAGAGGTA | | 52 |
| oligo 53 | Azide | AACGATTCGAGAACGTGACTGCNNNNNNNNNNNNCTGTGTTCCCACGTATCAATAGAGGTA | | 53 |
| oligo 54 | Azide | AACGATTCGAGAACGTGACTGCNNNNNNNNNNNNGGACATTCCCACGTATCAATAGAGGTA | | 54 |
| oligo 55 | Azide | AACGATTCGAGAACGTGACTGCNNNNNNNNNNNNCAAAGTTCCCACGTATCAATAGAGGTA | | 55 |
| oligo 56 | | GCGAAACCTGGTCCGGTATCNNNNNNNNNNNNNNNNGATGTTGAAGGCT | | 56 |
| oligo 57 | phosphorylation | GCCTTCAACATCTTGCGTGTGATTCCTAGTAATG | | 57 |
| oligo 58 | | GCGTGTGATTCCTAGTAATGCGATTCGAGAACGTGACTGC | | 58 |
| oligo 59 | | GCTATTATGATGTCTCAGGTCGATTCGAGAACGTGACTGC | | 59 |
| oligo 60 | | GCGAAACCTGGTCCGGTATCNNNNNNNNNNNNNNNNTGCTATTATGATGTCTCAGGT | | 60 |
| oligo 61 | | CGATTCGAGAACGTGACTGCNNNNNNNNNNNNNNNNCCCACGTATCAATAGAGGTA | | 61 |
| oligo 62 | | CTAGTGCTGGATGATCGTCCAAAA | inverted dT | 62 |

The invention claimed is:

1. A method for studying constituents of a molecular complex by labelling the molecules belonging to the same complex with at least one set of molecular constructs, wherein each member of the set comprises a Unique Identifying Sequence (UIS), which is a nucleic acid sequence unique for each member of the set, and at least one Common Tag Sequence (CTS), which is a nucleic acid sequence common to all members of the set, by:

attaching the molecular construct to the complex by ligating or hybridizing the molecular construct to a nucleic acid molecule of the complex, or ligating or hybridizing the molecular construct to a nucleic acid linked to an affinity binder that binds specifically to a constituent of the complex, labelling the molecules belonging to the same complex by using the molecular construct as primers or templates in a nucleic acid polymerization reaction, and analyzing the composition of the molecular complex by analyzing the combinations of UISs and CTSs, wherein the step of labelling the molecules belonging to the same complex by using the molecular construct is performed by PCR in a confined volume of <100 nl, and wherein a CTS of one set of molecular constructs are amplified in a first PCR and serves as primers to extend on nucleic acid molecules of the molecular complex and the other set of molecular tags by polymerization, said method further comprising pooling the polymerized nucleic acid molecules from all individual confined volumes of aqueous solution;

sequencing the pooled polymerized nucleic acid molecules;

using the extended set of molecular constructs to analyse the composition of the amplified set of molecular constructs from each confined volume; and using the amplified set of molecular constructs to decode the complex composition of each molecular complex.

2. The method according to claim 1, wherein each member of the set of molecular constructs comprises a plurality of said UIS and a plurality of said CTS, the method comprising the steps providing a first set of molecular constructs, wherein each member of the set comprises an affinity binder that binds specifically to a constituent of the molecular complex; and a nucleic acid comprising, in 5' to 3' direction, a Complex Constituent Unique Identifying Sequence (CCUIS), which is unique for each affinity binder in the set, and a common primer hybridization sequence, which is common to all members of the set and complementary to the CTS of the molecular construct tags;

allowing the affinity binder parts of the first set of molecular constructs to bind to the constituents of the molecular complex;

providing a second set of molecular constructs, wherein each member comprises a DNA concatemer containing identical copies of a nucleic acid molecule, comprising a 5'-CTS at the 5' end, a UIS comprising degenerate bases, and a 3'-CTS at the 3'end;

allowing the CTS of the second molecular constructs to hybridize to the CTS of the first molecular constructs on the complex;

extending the nucleic acid part of the first set of molecular construct on the hybridized second set of molecular construct by using a DNA polymerase without strand displacement activity;

sequencing the extension products; and analyzing the produced pool of extension products comprising different CCUIS, UIS, and CTS.

3. Method according to claim 1, for obtaining a set of identifiable nucleic acid molecules from each original nucleic acid molecule in a set of original nucleic acid molecules, comprising the steps providing a first set of nucleic acid constructs, wherein each member of the set comprise, in 3' to 5' direction, a Unique Identifying Sequence ("UIS"), which is unique for each member of the set, and a first common tag sequence ("CTS"), which is common to all members of the set;

ligating the first set of nucleic acid constructs to the 5'-end of the original nucleic acid molecules;

providing a second set of nucleic acid constructs, wherein each member of the set comprises a second CTS, which is common to all members of the set;

ligating the second set of nucleic acid constructs to the 3'-end of the original nucleic acid molecules;

amplifying the original nucleic acid molecules by PCR using primers hybridizing to the first and second CTS, and obtaining single stranded amplified nucleic acid molecules;

providing a third set of nucleic acid constructs, wherein each member of the set comprise, in 5' to 3' direction, a common polymerization primer sequence, which is common to all members of the set, and a 3' end comprising degenerate bases;

allowing the third set of nucleic acid constructs to hybridize to the amplified single stranded nucleic acid molecules at sites having a sequence complementary to the random nucleotide sequences;

providing a nucleic acid dependent polymerase and initiating a polymerization reaction producing a result set of nucleic acid molecules, wherein each member of the result set comprises, in the 5' to 3' direction: the common polymerization primer, a subsequence of one member of the set of original nucleic acid molecules, a Unique Identifying Sequence, and the first CTS; whereby the members of the result set having the same Unique Identifying Sequence originates from the same original nucleic acid molecule.

4. Method according to claim 1, for determining constituents in a molecular complex present in an aqueous solution, wherein said molecular complex comprise an original nucleic acid molecule, comprising the steps providing a first set of nucleic acid constructs, wherein each member of the set comprise, in 3' to 5' direction, a Original Nucleic Acid Unique Identifying Sequence (ONAUIS), which is unique for each member of the set, and a third CTS, which is common to all members of the set;

ligating the first set of nucleic acid constructs to the 5'-end of the original nucleic acid molecules;

providing a second set of nucleic acid constructs, wherein each member of the set comprises the first CTS present in the set of molecular constructs, and which is common to all members of the second set of nucleic acid constructs;

ligating the second set of nucleic acid constructs to the 3'-end of the original nucleic acid molecules;—providing at least one set of molecular constructs, wherein each member of one set comprises an affinity binder that binds specifically to a constituent of the molecular complex; and a nucleic acid comprising, in 5' to 3' direction, a first common tag sequence ("CTS"), which is common to all members of the set, a Complex Constituent Unique Identifying Sequence ("CCUIS"), which is unique for each affinity binder in the set, and a second CTS, which is common to all members of the set;

attaching the molecular construct to constituent of the molecular complex;

confining a volume of the aqueous solution containing no or one individual molecular complex;

amplifying in the confined volume the original nucleic acid molecule with added

ONAUIS and CTSs, by PCR using primers hybridizing to the first and third CTS, and obtaining single stranded amplified nucleic acid molecules by using an excess of primer hybridizing to the third CTS;

providing a primer for a nucleic acid dependent polymerase, said primer hybridizing to the second CTS of the nucleic acid in the set of molecular constructs;

providing a nucleic acid dependent polymerase and initiating a polymerization reaction producing a result set of nucleic acid molecules, wherein each member of the result set comprises, in the 5' to 3' direction: the second CTS, a CCUIS, the first CTS, a subsequence of the original nucleic acid molecule, a ONAUIS, and the third CTS;

pooling the polymerized nucleic acid molecules from all individual confined volumes of aqueous solution;

sequencing the pooled polymerized nucleic acid molecules;

determining the identity and/or relative content of constituents of the molecular complex from the presence and/or relative content of nucleic acid molecules comprising a CCUIS associated with the respective constituents of the molecular complex.

5. Method according to claim 1, for determining constituents in a molecular complex present in an aqueous solution, comprising the steps providing at least one set of molecular constructs, wherein each member of one set comprises an affinity binder that binds specifically to a constituent of the molecular complex; and a nucleic acid comprising, in 5' to 3' direction, a first Common Tag Sequence ("CTS") (PI), which is common to all members of the set, a Complex Constituent Unique Identifying Sequence (CCUIS), which is unique for each affinity binder in the set, and a second CTS (P4), which is common to all members of the set;

attaching the molecular construct to constituent of the molecular complex;

providing a first set of nucleic acid constructs, wherein each member of the set comprises, in 5' to 3' direction, the first CTS (PI), which is common to all members of the set, a Set 1 Unique Identifying Sequence (S1UIS), which is unique for each member of the set, and the second CTS (P4), which is common to all members of the set;

providing a second set of nucleic acid constructs, wherein each member of the set comprises, in 5' to 3' direction, a third CTS (P2), which is common to all members of the set, a Set 2 Unique Identifying Sequence (S2UIS), which is unique for each member of the set, and a fourth CTS (P3), which is common to all members of the set;

providing a third set of nucleic acid constructs, wherein the members of the set comprise, in 3' to 5' direction, a sequence consisting the second CTS (P4), and a sequence consisting the third CTS (P2);

providing a fourth set of nucleic acid constructs, wherein the members of the set consists the first CTS (PI);

providing a fifth set of nucleic acid constructs, wherein the members of the set consist of a sequence reverse complementary (rc) to the fourth CTS (P3(rc));

confining a volume of the aqueous solution such that the volume contains no (0) or one (1) individual molecular complex, a random number of members of the first and second sets of nucleic acid constructs, and larger number of members of the third, fourth and fifth sets of nucleic acid constructs;

amplifying in the confined volume the members of the second set of nucleic acid constructs, by PCR using members of the third and fifth set of nucleic acid constructs as primers and obtaining single stranded amplified nucleic acid molecules by using an excess of members of the fifth set of nucleic acid constructs, which single stranded nucleic acid molecules comprise in 5' to 3' direction, P3 (rc)-S2UIS (rc)-P2(rc)-P4(rc);

amplifying in the confined volume the members of the first set of nucleic acid constructs and the nucleic acids attached to the affinity binders, by PCR using the obtained single stranded amplified nucleic acid molecules and members of the fourth set of nucleic acid constructs as primers, thereby obtaining a mixture of amplified nucleic acid molecules of general sequence P1-[CCUIS/S1UIS]-P4-P2-S2UIS-P3;

pooling the polymerized nucleic acid molecules from all individual confined volumes of aqueous solution;

sequencing the pooled polymerized nucleic acid molecules;

identifying all the S2 UISs in each confined volume by analysing the sequencing reads comprising PI-S1UIS-P4-P2-S2UIS-P3;

identifying all the CCUISs in each confined volume by analysing the sequencing reads comprising P1-CCUIS-P4-P2-S2UIS-P3 with the identified S2UISs of each confined volume;

determining the identity and/or relative content of constituents of the molecular complex from the presence and/or relative content of nucleic acid molecules comprising a CCUIS associated with the respective constituents of the molecular complex.

6. The method according to claim 5, wherein the first and second sets of nucleic constructs can be attached to the components of the molecular complex.

7. The method according to claim 6, wherein the second sets of nucleic constructs are designed to be attached to only some molecular complexes in a mixture with certain features.

8. The method according to claim 4, wherein the confined volume is <100 nl.

9. The method according to claim 8, wherein the confined volume is a water in oil emulsion.

10. The method according to claim 1, wherein the ratio between forward and reverse primers in the PCR step favours single stranded or double stranded PCR products.

11. The method according to claim 1, comprising use of reverse primers with varying 5' end sequences in the PCR step, to obtain varying 3' end sequences of the PCR product.

12. The method according to claim 5, wherein the confined volume is <100 nl.

* * * * *

SEQUENCE LISTING

<160> NUMBER OF SEQ ID NOS: 65

<210> SEQ ID NO 1
<211> LENGTH: 48
<212> TYPE: DNA

<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (21)..(35)
<223> OTHER INFORMATION: n is a, c, g, or t

<400> SEQUENCE: 1
gcgaaacctg gtccggtatc nnnnnnnnnn nnnnngatgt tgaaggca         48

<210> SEQ ID NO 2
<211> LENGTH: 34
<212> TYPE: DNA
<213> ORGANISM: Artificial Sequence
<220> FEATURE:
<223> OTHER INFORMATION: Molecular construct tag for proximity barcoding

<400> SEQUENCE: 2
gccttcaaca tcttgcgtgt gattcctagt aatg                       34

<210> SEQ ID NO 3
<211> LENGTH: 20
<212> TYPE: DNA
<213> ORGANISM: Artificial Sequence
<220> FEATURE:
<223> OTHER INFORMATION: Molecular construct tag for proximity barcoding

<400> SEQUENCE: 3
gcgaaacctg gtccggtatc                                       20

<210> SEQ ID NO 4
<211> LENGTH: 20
<212> TYPE: DNA
<213> ORGANISM: Artificial Sequence
<220> FEATURE:
<223> OTHER INFORMATION: Molecular construct tag for proximity barcoding

<400> SEQUENCE: 4
cattactagg aatcacacgc                                       20

<210> SEQ ID NO 5
<211> LENGTH: 26
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (21)..(26)
<223> OTHER INFORMATION: n is a, c, g, or t

<400> SEQUENCE: 5
tacctctatt gatacgtggg nnnnnn                                26

<210> SEQ ID NO 6
<211> LENGTH: 20
<212> TYPE: DNA
<213> ORGANISM: Artificial Sequence
<220> FEATURE:
<223> OTHER INFORMATION: Molecular construct tag for proximity barcoding

<400> SEQUENCE: 6
tacctctatt gatacgtggg                                       20

<210> SEQ ID NO 7
<211> LENGTH: 57

```
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 7
gcgaaacctg gtccggtatc tttaggnnnn nnnnnntgct attatgatgt ctcaggt      57

<210> SEQ ID NO 8
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 8
gcgaaacctg gtccggtatc attccannnn nnnnnntgct attatgatgt ctcaggt      57

<210> SEQ ID NO 9
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 9
gcgaaacctg gtccggtatc gctcaannnn nnnnnntgct attatgatgt ctcaggt      57

<210> SEQ ID NO 10
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 10
gcgaaacctg gtccggtatc catcccnnnn nnnnnntgct attatgatgt ctcaggt      57

<210> SEQ ID NO 11
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 11
gcgaaacctg gtccggtatc aagcggnnnn nnnnnntgct attatgatgt ctcaggt      57

<210> SEQ ID NO 12
```

```
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 12
gcgaaacctg gtccggtatc aataaannnn nnnnnntgct attatgatgt ctcaggt      57

<210> SEQ ID NO 13
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 13
gcgaaacctg gtccggtatc gaggagnnnn nnnnnntgct attatgatgt ctcaggt      57

<210> SEQ ID NO 14
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 14
gcgaaacctg gtccggtatc ggtacannnn nnnnnntgct attatgatgt ctcaggt      57

<210> SEQ ID NO 15
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 15
gcgaaacctg gtccggtatc agcgagnnnn nnnnnntgct attatgatgt ctcaggt      57

<210> SEQ ID NO 16
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 16
gcgaaacctg gtccggtatc gtcggtnnnn nnnnnntgct attatgatgt ctcaggt      57
```

```
<210> SEQ ID NO 17
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 17
gcgaaacctg gtccggtatc atttgcnnnn nnnnnntgct attatgatgt ctcaggt      57

<210> SEQ ID NO 18
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 18
gcgaaacctg gtccggtatc aggactnnnn nnnnnntgct attatgatgt ctcaggt      57

<210> SEQ ID NO 19
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 19
gcgaaacctg gtccggtatc aggactnnnn nnnnnntgct attatgatgt ctcaggt      57

<210> SEQ ID NO 20
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 20
gcgaaacctg gtccggtatc tcgtaannnn nnnnnntgct attatgatgt ctcaggt      57

<210> SEQ ID NO 21
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 21
gcgaaacctg gtccggtatc ccagacnnnn nnnnnntgct attatgatgt ctcaggt      57
```

-continued

<210> SEQ ID NO 22
<211> LENGTH: 32
<212> TYPE: DNA
<213> ORGANISM: Artificial Sequence
<220> FEATURE:
<223> OTHER INFORMATION: Molecular construct tag for proximity barcoding

<400> SEQUENCE: 22
ctctctctct ctctctctct ctctctctct ct                         32

<210> SEQ ID NO 23
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 23
gcgaaacctg gtccggtatc ttggacnnnn nnnnnntgct attatgatgt ctcaggt    57

<210> SEQ ID NO 24
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 24
gcgaaacctg gtccggtatc ctgtgtnnnn nnnnnntgct attatgatgt ctcaggt    57

<210> SEQ ID NO 25
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 25
gcgaaacctg gtccggtatc ggacatnnnn nnnnnntgct attatgatgt ctcaggt    57

<210> SEQ ID NO 26
<211> LENGTH: 57
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (27)..(36)
<223> OTHER INFORMATION: n is a, c, g, or t

<400> SEQUENCE: 26
gcgaaacctg gtccggtatc caaagtnnnn nnnnnntgct attatgatgt ctcaggt    57

<210> SEQ ID NO 27
<211> LENGTH: 100

```
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(37)
<223> OTHER INFORMATION: n is a, c, g, or t

<400> SEQUENCE: 27
gctattatga tgtctcaggt aannnnnnnn nnnnnnnttt cccacgtatc aatagaggta      60
gcagtcacgt tctcgaatcg ctagtgctgg atgatcgtcc                          100

<210> SEQ ID NO 28
<211> LENGTH: 36
<212> TYPE: DNA
<213> ORGANISM: Artificial Sequence
<220> FEATURE:
<223> OTHER INFORMATION: Molecular construct tag for proximity barcoding

<400> SEQUENCE: 28
ctgagacatc ataatagcgg acgatcatcc agcact                               36

<210> SEQ ID NO 29
<211> LENGTH: 20
<212> TYPE: DNA
<213> ORGANISM: Artificial Sequence
<220> FEATURE:
<223> OTHER INFORMATION: Molecular construct tag for proximity barcoding

<400> SEQUENCE: 29
cgattcgaga acgtgactgc                                                 20

<210> SEQ ID NO 30
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 30
ccatctcatc cctgcgtgtc tccgactcag ggtttggcga aacctggtcc ggtatc          56

<210> SEQ ID NO 31
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 31
ccatctcatc cctgcgtgtc tccgactcaa tggcgggcga aacctggtcc ggtatc          56

<210> SEQ ID NO 32
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 32
ccatctcatc cctgcgtgtc tccgactcat tcataggcga aacctggtcc ggtatc          56

<210> SEQ ID NO 33
<211> LENGTH: 56
<212> TYPE: DNA
```

```
<213> ORGANISM: Artificial Sequence
<220> FEATURE:
<223> OTHER INFORMATION: Molecular construct tag for proximity barcoding

<400> SEQUENCE: 33
ccatctcatc cctgcgtgtc tccgactcaa acgccggcga aacctggtcc ggtatc     56

<210> SEQ ID NO 34
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 34
ccatctcatc cctgcgtgtc tccgactcag gctgcggcga aacctggtcc ggtatc     56

<210> SEQ ID NO 35
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 35
ccatctcatc cctgcgtgtc tccgactcag gctgcggcga aacctggtcc ggtatc     56

<210> SEQ ID NO 36
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 36
ccatctcatc cctgcgtgtc tccgactcaa gatggggcga aacctggtcc ggtatc     56

<210> SEQ ID NO 37
<211> LENGTH: 56
<212> TYPE: DNA
<213> ORGANISM: Artificial Sequence
<220> FEATURE:
<223> OTHER INFORMATION: Molecular construct tag for proximity barcoding

<400> SEQUENCE: 37
ccatctcatc cctgcgtgtc tccgactcag taatgggcga aacctggtcc ggtatc     56

<210> SEQ ID NO 38
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 38
cctctctatg ggcagtcggt gatcatgatt acctctattg atacgtggg            49

<210> SEQ ID NO 39
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 39
cctctctatg ggcagtcggt gattgtgcgt acctctattg atacgtggg            49
```

<210> SEQ ID NO 40
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 40
cctctctatg ggcagtcggt gatgcaggat acctctattg atacgtggg        49

<210> SEQ ID NO 41
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 41
cctctctatg ggcagtcggt gattctacct acctctattg atacgtggg        49

<210> SEQ ID NO 42
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 42
cctctctatg ggcagtcggt gatagtcgtt acctctattg atacgtggg        49

<210> SEQ ID NO 43
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 43
cctctctatg ggcagtcggt gatcgtggct acctctattg atacgtggg        49

<210> SEQ ID NO 44
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 44
cctctctatg ggcagtcggt gatgcgtcct acctctattg atacgtggg        49

<210> SEQ ID NO 45
<211> LENGTH: 49
<212> TYPE: DNA
<213> ORGANISM: Artificial Sequence
<220> FEATURE:
<223> OTHER INFORMATION: Molecular construct tag for proximity barcoding

<400> SEQUENCE: 45
cctctctatg ggcagtcggt gatgaacgct acctctattg atacgtggg        49

<210> SEQ ID NO 46
<211> LENGTH: 30
<212> TYPE: DNA
<213> ORGANISM: Artificial Sequence
<220> FEATURE:

-continued

<223> OTHER INFORMATION: Molecular construct tag for proximity barcoding

<400> SEQUENCE: 46
ccatctcatc cctgcgtgtc tccgactcag                                              30

<210> SEQ ID NO 47
<211> LENGTH: 23
<212> TYPE: DNA
<213> ORGANISM: Artificial Sequence
<220> FEATURE:
<223> OTHER INFORMATION: Molecular construct tag for proximity barcoding

<400> SEQUENCE: 47
cctctctatg ggcagtcggt gat                                                     23

<210> SEQ ID NO 48
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 48
aacgattcga gaacgtgact gcnnnnnnnn nntttaggtc ccacgtatca atagaggta              59

<210> SEQ ID NO 49
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 49
aacgattcga gaacgtgact gcnnnnnnnn nnattccatc ccacgtatca atagaggta              59

<210> SEQ ID NO 50
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 50
aacgattcga gaacgtgact gcnnnnnnnn nngctcaatc ccacgtatca atagaggta              59

<210> SEQ ID NO 51
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 51
aacgattcga gaacgtgact gcnnnnnnnn nncatccctc ccacgtatca atagaggta         59

<210> SEQ ID NO 52
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 52
aacgattcga gaacgtgact gcnnnnnnnn nnttggactc ccacgtatca atagaggta         59

<210> SEQ ID NO 53
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 53
aacgattcga gaacgtgact gcnnnnnnnn nnctgtgttc ccacgtatca atagaggta         59

<210> SEQ ID NO 54
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 54
aacgattcga gaacgtgact gcnnnnnnnn nnggacattc ccacgtatca atagaggta         59

<210> SEQ ID NO 55
<211> LENGTH: 59
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (23)..(32)
<223> OTHER INFORMATION: n is a, c, g, or t

<400> SEQUENCE: 55
aacgattcga gaacgtgact gcnnnnnnnn nncaaagttc ccacgtatca atagaggta         59

<210> SEQ ID NO 56
<211> LENGTH: 48
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (21)..(35)
<223> OTHER INFORMATION: n is a, c, g, or t

<400> SEQUENCE: 56
gcgaaacctg gtccggtatc nnnnnnnnnn nnnnngatgt tgaaggct           48

<210> SEQ ID NO 57
<211> LENGTH: 34
<212> TYPE: DNA
<213> ORGANISM: Artificial Sequence
<220> FEATURE:
<223> OTHER INFORMATION: Molecular construct tag for proximity barcoding

<400> SEQUENCE: 57
gccttcaaca tcttgcgtgt gattcctagt aatg                          34

<210> SEQ ID NO 58
<211> LENGTH: 40
<212> TYPE: DNA
<213> ORGANISM: Artificial Sequence
<220> FEATURE:
<223> OTHER INFORMATION: Molecular construct tag for proximity barcoding

<400> SEQUENCE: 58
gcgtgtgatt cctagtaatg cgattcgaga acgtgactgc                    40

<210> SEQ ID NO 59
<211> LENGTH: 40
<212> TYPE: DNA
<213> ORGANISM: Artificial Sequence
<220> FEATURE:
<223> OTHER INFORMATION: Molecular construct tag for proximity barcoding

<400> SEQUENCE: 59
gctattatga tgtctcaggt cgattcgaga acgtgactgc                    40

<210> SEQ ID NO 60
<211> LENGTH: 56
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (21)..(35)
<223> OTHER INFORMATION: n is a, c, g, or t

<400> SEQUENCE: 60
gcgaaacctg gtccggtatc nnnnnnnnnn nnnnntgcta ttatgatgtc tcaggt   56

<210> SEQ ID NO 61
<211> LENGTH: 55
<212> TYPE: DNA
<213> ORGANISM: Artificial Sequence
<220> FEATURE:
<223> OTHER INFORMATION: Molecular construct tag for proximity barcoding
<220> FEATURE:
<221> NAME/KEY: misc_feature
<222> LOCATION: (21)..(35)
<223> OTHER INFORMATION: n is a, c, g, or t

<400> SEQUENCE: 61
cgattcgaga acgtgactgc nnnnnnnnnn nnnnncccac gtatcaatag aggta    55

<210> SEQ ID NO 62
<211> LENGTH: 24
<212> TYPE: DNA
<213> ORGANISM: Artificial Sequence
<220> FEATURE:
<223> OTHER INFORMATION: Molecular construct tag for proximity barcoding

```
<400> SEQUENCE: 62
ctagtgctgg atgatcgtcc aaaa                                          24

<210> SEQ ID NO 63
<211> LENGTH: 15
<212> TYPE: DNA
<213> ORGANISM: Artificial Sequence
<220> FEATURE:
<223> OTHER INFORMATION: Unique Identifying Sequence (UIS) - synthetic
      sequence

<400> SEQUENCE: 63
tggggttagc aagtc                                                    15

<210> SEQ ID NO 64
<211> LENGTH: 15
<212> TYPE: DNA
<213> ORGANISM: Artificial Sequence
<220> FEATURE:
<223> OTHER INFORMATION: UIS N1 - synthetic sequence

<400> SEQUENCE: 64
gcaccctaaa cgatg                                                    15

<210> SEQ ID NO 65
<211> LENGTH: 15
<212> TYPE: DNA
<213> ORGANISM: Artificial Sequence
<220> FEATURE:
<223> OTHER INFORMATION: UIS Nm - synthetic sequence

<400> SEQUENCE: 65
ttgaagactc gcgat                                                    15
```